United States Patent
Zamvil et al.

(10) Patent No.: US 9,234,017 B2
(45) Date of Patent: Jan. 12, 2016

(54) AQUAPORIN-4 PEPTIDE COMPOSITIONS AND METHODS OF USE THEREOF

(71) Applicant: The Regents of the University of California, Oakland, CA (US)

(72) Inventors: Scott S. Zamvil, Palo Alto, CA (US); Michel Varrin-Doyer, San Francisco, CA (US); Bruce Anthony Campbell Cree, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/102,294

(22) Filed: Dec. 10, 2013

(65) Prior Publication Data

US 2014/0199333 A1 Jul. 17, 2014

Related U.S. Application Data

(60) Provisional application No. 61/735,675, filed on Dec. 11, 2012.

(51) Int. Cl.

| C07K 14/47 | (2006.01) |
|---|---|
| C07K 7/06 | (2006.01) |
| A61K 39/00 | (2006.01) |
| C07K 7/08 | (2006.01) |
| G01N 33/50 | (2006.01) |
| C07K 14/705 | (2006.01) |

(52) U.S. Cl.
CPC .............. *C07K 14/47* (2013.01); *A61K 39/0008* (2013.01); *C07K 7/06* (2013.01); *C07K 7/08* (2013.01); *C07K 14/705* (2013.01); *G01N 33/505* (2013.01); *G01N 33/5094* (2013.01); *G01N 2800/28* (2013.01)

(58) Field of Classification Search
CPC ............ C07K 7/06; C07K 7/08; C07K 14/47; C07K 14/705; G01N 33/505; G01N 33/5094; G01N 2800/28; A61K 39/0008
See application file for complete search history.

(56) References Cited

PUBLICATIONS

Acosta-Rodriguez, et al. (2007) "Interleukins 1beta and 6 but not transforming growth factor-beta are essential for the differentiation of interleukin 17-producing human T helper cells" Nat Immunol. 8(9):942-9.
Brum, et al. (2010) "HLA-DRB association in neuromyelitis optica is different from that observed in multiple sclerosis" Mult Scler 16(1):21-9.
Deschamps, et al. (2011) "Different HLA class II (DRB1 and DQB1) alleles determine either susceptibility or resistance to NMO and multiple sclerosis among the French Afro-Caribbean population" Mult Scler 17(1):24-31.
Fujinami & Oldstone (1985) "Amino acid homology between the encephalitogenic site of myelin basic protein and virus: mechanism for autoimmunity" Science 230(4729):1043-5.
GenBank Accession No. AAH22286.1 "Aquaporin 4 [Homo sapiens]" dated Jul. 15, 2006.
GenBank Accession No. ZP_02431563 "hypothetical protein CLOSCI_01783 [*Clostridium scindens* ATCC 35704]" dated Nov. 27, 2012.
GenBank Accession No. ZP_02630305.1 "ABC transporter, permease/ATP-binding protein [*Clostridium perfringens* E str. JGS1987]" dated Dec. 10, 2010.
GenBank Accession No. ZP_02634520.1 "ABC transporter, permease/ATP-binding protein [*Clostridium perfringens* B str. ATCC 3626]" dated Dec. 10, 2010.
GenBank Accession No. ZP_02638213.1 "ABC transporter, permease/ATP-binding protein [*Clostridium perfringens* CPE str. F4969]" dated Dec. 10, 2010.
GenBank Accession No. ZP_02952885.1 "ABC transporter, permease/ATP-binding protein [*Clostridium perfringens* D str. JGS1721]" dated Nov. 10, 2010.
GenBank Accession No. ZP_02995934 "hypothetical protein CLOSPO_03057 [*Clostridium sporogenes* ATCC 15579]" dated Nov. 27, 2012.
GenBank Accession No. ZP_03776873.1 "hypothetical protein CLOHYLEM_03921 [*Clostridium hylemonae* DSM 15053]" dated Nov. 27, 2012.
Jacob, et al. (2008) "Treatment of neuromyelitis optica with rituximab: retrospective analysis of 25 patients" Arch Neurol. 65(11):1443-8.
Kalluri Sr, et al. (2011) "Functional characterization of aquaporin-4 specific T cells: towards a model for neuromyelitis optica." PLoS One 6(1):e16083.
Katzman, et al. (2011) "Differential requirements for Th1 and Th17 responses to a systemic self-antigen" J Immunol. 186(8):4668-73.
Kuchroo, et al. (1995) "B7-1 and B7-2 costimulatory molecules activate differentially the Th1/Th2 developmental pathways: application to autoimmune disease therapy" Cell 80(5):707-18.
Lucchinetti, et al. (2002) "A role for humoral mechanisms in the pathogenesis of Devic's neuromyelitis optica" Brain 125(Pt 7):1450-61.
Matsushita, et al. (2009) "Association of the HLA-DPB1*0501 allele with anti-aquaporin-4 antibody positivity in Japanese patients with idiopathic central nervous system demyelinating disorders" Tissue Antigens 73(2):171-6.

(Continued)

*Primary Examiner* — Robert Landsman
(74) *Attorney, Agent, or Firm* — Carol L. Francis; Shweta Chandra; Bozicevic, Field & Francis LLP

(57) ABSTRACT

The present disclosure provides human Aquaporin 4 (AQP4) peptides and peptides having homology to human Aquaporin 4 (AQP4) peptides. Also provided herein are methods for using human AQP4 peptides and peptides homologous to human AQP4 peptides for diagnosing and/or treating Neuromyelitis Optica.

24 Claims, 18 Drawing Sheets

(56) References Cited

PUBLICATIONS

Nelson, et al. (2010) "Immunodominant T cell determinants of aquaporin-4, the autoantigen associated with neuromyelitis optica" PLoS One 5(11):e15050 1-9.

Owens G, et al. (2011) "Mutagenesis of aquaporin-4 extracellular domains defines binding patterns of neuromyelitis optica intrathecal IgG" Mult Scler. 17(10 Suppl):S291-S292.

Uzawa, et al. (2010) "Cytokine and chemokine profiles in neuromyelitis optica: significance of interleukin-6" Mult Scler 16(12):1443-52.

Warabi, et al. (2006) "Characterization of the T cell receptor repertoire in the Japanese neuromyelitis optica: T cell activity is up-regulated compared to multiple sclerosis" J Neurol Sci. 249(2):145-52.

Wingerchuk et al. (2006) "Revised diagnostic criteria for neuromyelitis optica" Neurology 66(10):1485-9.

Wucherpfennig & Strominger (1995) "Molecular mimicry in T cell-mediated autoimmunity: viral peptides activate human T cell clones specific for myelin basic protein" Cell. 80(5):695-705.

Zamvil, et al. (1986) "T-cell epitope of the autoantigen myelin basic protein that induces encephalomyelitis" Nature 324(6094):258-60.

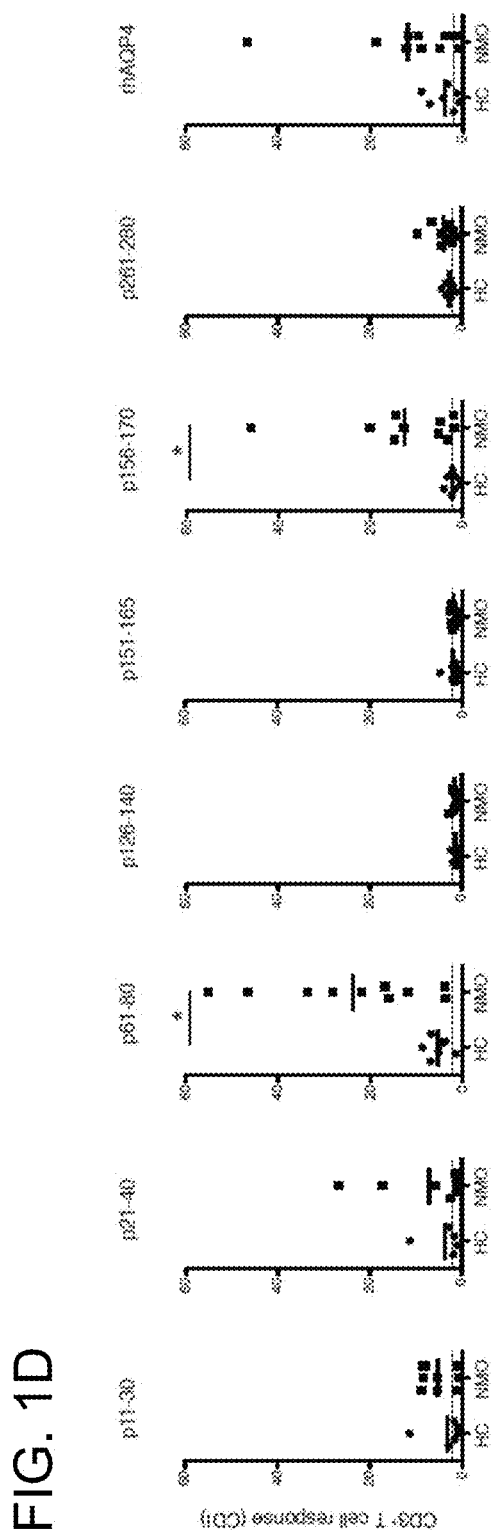

FIG. 3C

AQP4 p63-76        EKP LPVDMVLISL C
                       68        75

ABC transporter permease    F I I LPVSMVLISL V
p204-217 (Clostridium Perfringens)    207        216

```
  1 MSDRPTARRW GKCGPLCTRE NIMVAFKGVW TQAFWKAVTA EFLAMLIFVL LSLGSTINWG
 61 GTEKPLPVDM VLISLCFGLS IATMVQCFGH ISGGHINPAV TVAMVCTRKI SIAKSVFYIA
121 AQCLGAIIGA GILYLVTPPS VVGGLGVTMV HGNLTAGHGL LVELIITFQL VFTIFASCDS
181 KRTDVTGSIA LAIGFSVAIG HLFAINYTGA SMNPARSFGP AVIMGNWENH WIYWVGPIIG
241 AVLAGGLYEY VFCPDVEFKR REKEAFSKAA QQTKGSYMEV EDNRSQVETD DLILKPGVVH
301 VIDVDRGEEK KGKDQSGEVL SSV
```

FIG. 7

```
  1 MSKERKGGMG GPMGRMGGGP RAVEKAKDFK GTMKKLGVYL KPYSLSIAIV ILFAIGSAAF
 61 SIVGPKILGK ATTKIFEGLV QKITGVPDAS IDFGYIGNIA MILVALYLVS SLFGIIQSFI
121 MSGVAQKVSY NLRKQISEKM DTLPLNYFDT RTNGEVLSRI TNDVDTVNQT LNQSLSQIIT
181 SVVTLIGVLI MMFSISWIMT LATFIILPVS MVLISLVVKK SQKYFKSQQE YLGHLNGQVE
241 EVYGGHNIMK AFNREEASTK DFDELNNTLY KSAWKSQFLS GMMMPIMSFV GNLGYVLVSI
301 LGGWLTIKSV ITVGDIQAFI QYVRSFNQPI SQMAQVANIM QSTAAAAERV FEFLDEEDEV
361 KDPVNSVDPS EIRGEVEFED FHFGYNEDKI IINDFSVDVK PGQKVAIVGP TGAGKTTIVK
421 LLMRFYDINS GSIKIDGHDI RDFKRADLRN LFGMVLQDTW LFNGTIMENL RYGRLDATDA
481 EVKEAAKAAH VDHFVKTLPD GYNMVLNEEA SNISQGQKQL LTIARAFLKD PKLLILDEAT
541 SSVDTRTELL IQKAMEKLME GRTSFIIAHR LSTIRDADLI LVMKDGDIVE QGNHEELLEK
601 GGFYSSLYNS QFEQSSAS
```

AQUAPORIN-4 PEPTIDE COMPOSITIONS AND METHODS OF USE THEREOF

CROSS-REFERENCE TO RELATED APPLICATIONS

This application claims priority benefit to U.S. Provisional Application Ser. No. 61/735,675, filed Dec. 11, 2012, the disclosure of which is herein incorporated by reference in its entirety.

TECHNICAL FIELD

This present disclosure relates to peptides having homology to human Aquaporin 4 (AQP4) peptides and peptides having homology to human Aquaporin-4 (AQP-4) peptides and the use of theses peptides in diagnosing, and/or treating neuromyelitis optica (NMO).

INTRODUCTION

Neuromyelitis optica (NMO), or Devic's disease, is an autoimmune, inflammatory disorder of the optic nerves and spinal cord. The main symptoms of Devic's disease are loss of vision and spinal cord function. As for other etiologies of optic neuritis, the visual impairment usually manifests as decreased visual acuity, although visual field defects, or loss of color vision can occur in isolation or prior to formal loss of acuity. Spinal cord dysfunction can lead to muscle weakness, reduced sensation, or loss of bladder and bowel control. The damage in the spinal cord can range from inflammatory demyelination to necrotic damage of the white and grey matter. The inflammatory lesions in Devic's disease have been classified as type II lesions (complement mediated demyelination).

Attacks optic neuritis and transverse myelitis suffered by NMO patients are treated with short courses of high dosage intravenous corticosteroids such as methylprednisolone IV. When attacks progress or do not respond to corticosteroid treatment, plasmapheresis can be used. Commonly used immunosuppressant treatments include azathioprine (Imuran) plus prednisone, mycophenolate mofetil plus prednisone, Rituximab, Mitoxantrone, intravenous immunoglobulin (IVIG), and Cyclophosphamide.

The disease can be monophasic, i.e., a single episode with permanent remission. However, at least 85% of NMO patients have a relapsing form of the disease with repeated attacks of transverse myelitis and/or optic neuritis. In patients with the monophasic form of NMO, the transverse myelitis and optic neuritis occur simultaneously or within days of each other. On the other hand, patients with the relapsing form of NMO are more likely to have weeks or months between the initial attacks and to have better motor recovery after the initial transverse myelitis event. Relapses usually occur early with about 55% of patients having a relapse in the first year and 90% in the first 5 years.

Studies have suggested a role for T helper 17 (Th17) cells and autoantigens, including aquaporin and myelin proteins in the pathology of NMO. Th17 T cells are a subset of T helper cells, characterized by their production of interleukin 17 (IL-17). They are considered developmentally distinct from Th1 and Th2 cells and excessive amounts of the cells are thought to play a key role in autoimmune disease.

Provided herein are peptides, peptide compositions and methods useful in diagnosing and/or treating NMO.

SUMMARY

The present disclosure provides human Aquaporin 4 (AQP4) peptides and peptides having homology to human Aquaporin 4 (AQP4) peptides. Also provided herein are methods for using human AQP4 peptides and peptides homologous to human AQP4 peptides for diagnosing and/or treating Neuromyelitis Optica.

In certain embodiments, a composition is provided. The composition includes a peptide comprising a contiguous stretch of amino acids having the consensus amino acid sequence: Leu-Pro-$X^1$-$X^2$-Met-$X^3$-$X^4$-Ile-$X^5$-$X^6$ (SEQ ID NO:1), wherein the peptide is up to 50 amino acids in length, and wherein $X^1$ is Val (V) or Ile (I), $X^2$ is Ser (S) or Asp (D), $X^3$ is Val (V), Ile (I), or Gly (G), $X^4$ is Leu (L) or Ile (I), $X^5$ is Met (M) or Ser (S), and $X^6$ is Leu (L), Val (V), or Ala (A). In certain embodiments, $X^1$ is Val (V), $X^2$ is Ser (S) or Asp (D), $X^3$ is Val (V), $X^4$ is Leu (L), $X^5$ is Ser (S), and $X^6$ is Leu (L).

In another embodiment, a composition that includes a peptide comprising a contiguous stretch of amino acids having the consensus amino acid sequence: LPVXMVLISL (SEQ ID NO:2), wherein the peptide is up to 50 amino acids in length, and wherein X is Asp or Ser, is provided.

In another embodiment, a composition that includes a peptide comprising a contiguous stretch of amino acids having the consensus amino acid sequence: GILYLVTPPSVVG-GLGVTMV (SEQ ID NO:3), wherein the peptide is up to 50 amino acids in length, is provided.

In another embodiment, a composition that includes a peptide comprising a contiguous stretch of amino acids having the consensus amino acid sequence: SMNPARSFG-PAVIMGNWENH (SEQ ID NO:4), wherein the peptide is up to 50 amino acids in length, is provided.

In another embodiment, a composition that includes a peptide comprising a contiguous stretch of amino acids having the consensus amino acid sequence: AGHGLLVELIITFQL (SEQ ID NO:5), wherein the peptide is up to 50 amino acids in length, is provided.

In another embodiment, a composition that includes a peptide comprising a contiguous stretch of amino acids having the consensus amino acid sequence: RFKEAFSKAAQQT-KGSYMEV (SEQ ID NO:6), wherein the peptide is up to 50 amino acids in length, is provided.

In certain embodiments, the peptide may be 5-30 amino acids in length. In some embodiments, the peptide may be 10-20 amino acids in length.

In certain embodiments, a method of diagnosing Neuromyelitis Optica (NMO) in a subject is disclosed. The method may include contacting a sample from the subject with a peptide as disclosed herein; and measuring the number of T cells, wherein an increase in the number of T cells as compared to a control indicates that the subject has NMO.

In certain cases, the T cells may be T helper 17 (Th17) T cells. In certain cases, the T cells may be $CD4^+$ T cells. The peptide may be 5-30 amino acids in length. In certain cases, the peptide may be 10-20 amino acids in length.

In certain embodiments, a method for screening for candidate agents for inhibiting proliferation of T cells is provided. The method includes contacting a T cell obtained from a subject having Neuromyelitis Optica with a peptide as provided above, and a candidate agent; measuring the number of T cells, wherein a decrease in the number of T cells as compared to a control indicates that the candidate agent inhibits proliferation of T cells. In certain embodiments, the T cells may be T helper 17 (Th17) T cells. In certain embodiments, the T cells may be $CD4^+$ T cells. The peptide may be 5-30 amino acids in length. In certain cases, the peptide may be 10-20 amino acids in length.

A method for inducing immune tolerance to AQP-4 protein and fragments thereof in a subject is also provided. The method includes administering an effective dose of the composition set forth above to a subject, wherein the administering the peptide induces immune tolerance to AQP-4 protein and fragments thereof in the subject. The peptide may be 5-30 amino acids in length. In certain cases, the peptide may be 10-20 amino acids in length.

BRIEF DESCRIPTION OF THE DRAWINGS

FIG. 3A-3E illustrates the cross-reactivity between AQP4 p63-76 and *Clostridium perfringens* ABC transporter permease (ABC/TP) p204-217 (FIG. 3C, SEQ ID NO:7-8 from top to bottom).

FIG. 6 provides the amino acid sequence of human AQP-4 protein (GenBank Accession No. AAH22286.1, SEQ ID NO:9).

FIG. 7 provides the amino acid sequence of ABC-transporter permease protein of *Clostridium perfringens* (NCBI Reference Sequence: ZP_02952885.1, SEQ ID NO:10).

DETAILED DESCRIPTION OF EXEMPLARY EMBODIMENTS

Figure 1A:
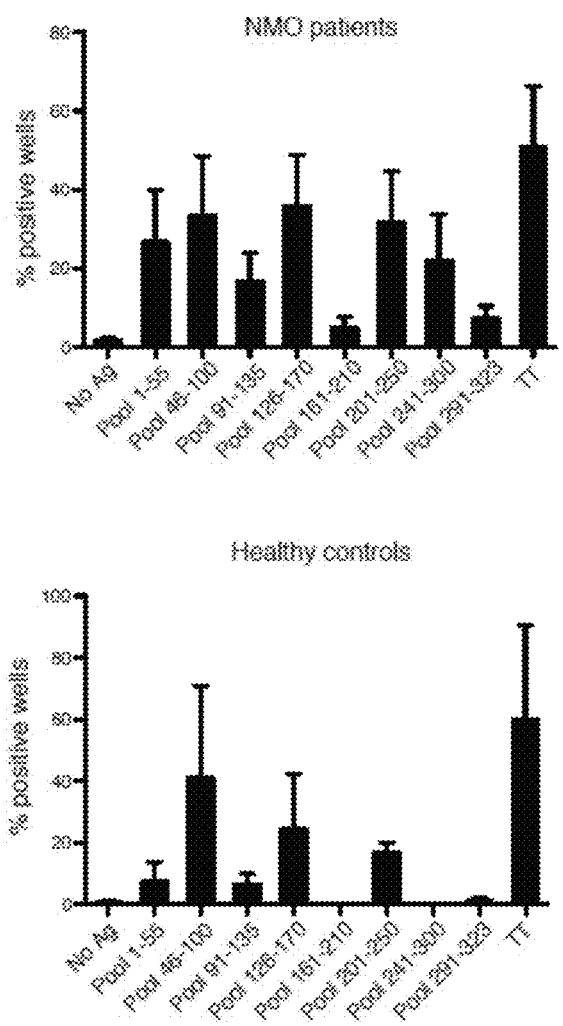
FIGS. 1A-1B and 1E-1F shows that T cells from NMO patients recognize discrete determinants of AQP4.

The present disclosure provides human Aquaporin 4 (AQP4) peptides and peptides having homology to human Aquaporin 4 (AQP4) peptides. Also provided herein are methods for using human AQP4 peptides and peptides homologous to human AQP4 peptides for diagnosing and/or treating Neuromyelitis Optica.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. To the extent such publications may set out definitions of a term that conflicts with the explicit or implicit definition of the present disclosure, the definition of the present disclosure controls.

It must be noted that as used herein and in the appended claims, the singular forms "a", "an", and "the" include plural referents unless the context clearly dictates otherwise. Thus, for example, reference to "a sample" includes a plurality of samples and reference to "a peptide" includes reference to one or more peptides, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The phrase "Aquaporin-4 (AQP-4) peptides" as used herein refers to peptides that are derived from amino acid sequence of human aquaporin-4. As such, AQP-4 peptides include peptides comprising a contiguous amino acid sequence that is identical to a contiguous amino acid sequence found in amino acid sequence of human aquaporin-4 (GenBank Accession No. AAH22286.1). An AQP-4 peptide may be 5-50 amino acids in length.

The phrase "AQP-4 homologous peptide" or a grammatical equivalent thereof, as used herein, refers to peptides that include a contiguous amino acid sequence that is at least 50%, at least 60%, at least 70%, at least 80%, or at least 90% identical to a contiguous amino acid sequence found in amino acid sequence of human AQP-4 protein. For example, a twenty amino acids long peptide that is at least 50% at least 60%, at least 70%, at least 80%, or at least 90% identical to a contiguous amino acid sequence found in amino acid sequence of human aquaporin-4 is an example of an AQP-4 homologous peptide.

The term "unit dosage form", as used herein, refers to physically discrete units suitable as unitary dosages for human and animal subjects, each unit containing a predetermined quantity of peptide(s) disclosed herein calculated in an amount sufficient to produce the desired effect in association with a pharmaceutically acceptable diluent, carrier or vehicle. The specifications for the unit dosage forms may depend on the particular peptide employed and the effect to be achieved, and the pharmacodynamics associated with each peptide in the host.

An "immunogen" is capable of inducing an immunological response against itself on administration to a mammal or due to autoimmune disease.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein refers to any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual", "subject", "host", and "patient", are used interchangeably herein and refer to any mammalian subject for whom diagnosis, treatment, or therapy is desired, particularly humans. Mammals other than humans can be advantageously used as subjects that represent animal models of inflammation. A subject can be male or female.

The term "a sample" as used herein refers to any biological sample that is isolated from a subject. A sample can include, without limitation, a single cell or multiple cells or cell fragments, such as, platelets, red blood cells, white blood cells or leucocytes, such as lymphocytes, e.g., B cell, T cells, endothelial cells, cell lysates, such as, whole cell lysates or a fraction of cell lysate; an aliquot of body fluid, whole blood, serum, plasma, synovial fluid, lymphatic fluid, ascites fluid, and interstitial or extracellular fluid; tissue biopsies. "Blood sample" can refer to whole blood or any fraction thereof, including blood cells, red blood cells, white blood cells or leucocytes, platelets, serum and plasma. Samples can be obtained from a subject by means including but not limited to venipuncture, biopsy, needle aspirate, scraping, surgical incision, or intervention or other means known in the art.

An "isolated" peptide is one which has been separated and/or recovered from a component of the environment in which it was produced. Contaminant components of its production environment are materials which would interfere with screening, diagnostic or therapeutic uses for the peptide, and may include chemicals, enzymes, hormones, and other proteinaceous or nonproteinaceous components. In certain cases, the peptides of the present disclosure are produced synthetically, for example, by chemical synthesis. In certain embodiments, the peptides are purified using standard purification procedures known in the art. Ordinarily, isolated peptide may be prepared by at least one purification step.

The term "agent" as used in the context of candidate agent refers to a chemical compound, a mixture of chemical compounds, a biological macromolecule, or an extract made from biological materials.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio. The effective amount for a patient may depend upon the type of patient, the patient's size and health, the nature and severity of the condition to be treated, the method of administration, the duration of treatment, the nature of concurrent therapy (if any), the specific formulations employed, and the like. The effective amount for a given subject can be determined by one of ordinary skill in the art using routine experimentation based on the information provided herein.

As used herein, the term "concurrent therapy" is used interchangeably with the terms "combination therapy" and "adjunct therapy", and will be understood to mean that the patient in need of treatment is treated or given another drug for the disease/disorder in conjunction with the compositions of the present disclosure. This concurrent therapy can be sequential therapy where the patient is treated first with one drug and then the other, or the two drugs are given simultaneously The term "pharmaceutically acceptable" refers to peptides and compositions containing peptides which are suitable for administration to humans and/or animals without undue adverse side effects such as toxicity, irritation and/or allergic response commensurate with a reasonable benefit/risk ratio.

The compositions comprising peptides disclosed herein may be administered to a patient by any method known in the art, including but not limited to, oral, topical, transdermal, parenteral, subcutaneous, intranasal, intramuscular, intraperitoneal, intravenous, intraocular, intravitreal, sub-retinal routes, including both local and systemic applications. In addition, the peptides disclosed herein may be formulated to provide delayed, controlled or sustained release using formulation techniques which are well known in the art.

OVERVIEW

The present disclosure provides peptides, including AQP-4 peptides derived from human AQP-4 protein and peptides homologous to AQP-4 peptides. As shown herein, AQP-4 peptide p61-80 includes a core sequence p63-76 (EKPLPVD-MVLISLC, SEQ ID NO:7) which is a T cell epitope. Peptides containing this core sequence or a sequence having at least 60% identity to the amino acid sequence of this core sequence result in proliferation of AQP-4 specific T cells in NMO patients.

Peptides

In certain embodiments, the present disclosure provides AQP-4 peptides and peptides homologous to AQP-4 peptides.

For example, examples of ABC-TP proteins from strains of *Clostridium perfringens, Clostridium scindens, Clostridium sporogens*, and *Clostridium hylemonae* are aligned in Table 1 over a region having sequence identity with an example of an AQP4 peptide, p66-75 (LPVDMVLISL, SEQ ID NO:11).

TABLE 1

| (SEQ ID NO: 11-15 from top to bottom) | | | |
|---|---|---|---|
| | | % Homology with AQP4 p66-75 | |
| AQP4 p66-75 | L P V D M V L I S L | | |
| C. perfringens | L P V <u>S</u> M V L I S L | 90% | Commensal and pathogenic |
| C. Scindens | L P V <u>S</u> M <u>G</u> L I S <u>V</u> | 70% | Commensal |
| C. Sporogenes | L P V <u>S</u> M <u>I</u> <u>I</u> <u>I</u> <u>M</u> L | 60% | Pathogenic |
| C. Hylemonae | L P <u>I</u> <u>S</u> M <u>G</u> L I S <u>A</u> | 60% | Commensal |

Accordingly, AQP-4 peptides comprise a contiguous stretch of amino acids having the consensus amino acid sequence:

$$\text{Leu-Pro-}X^1\text{-}X^2\text{-Met-}X^3\text{-}X^4\text{-Ile-}X^5\text{-}X^6 \quad \text{(Formula I)}$$

wherein $X^1$, $X^2$, $X^3$, $X^4$, $X^5$, and $X^6$ are any amino acid (SEQ ID NO:16), and wherein the peptide is up to 50 amino acids in length.

In certain embodiments, $X^1$ is Val (V) or Ile (I). In certain embodiments, $X^2$ is Ser (S) or Asp (D). In certain embodiments, $X^3$ is Val (V), Ile (I), or Gly (G). In certain embodiments, $X^4$ is Leu (L) or Ile (I). In certain embodiments, $X^5$ is Met (M) or Ser (S). In certain embodiments, $X^6$ is Leu (L), Val (V), or Ala (A). In certain embodiments, $X^1$ is Val (V), $X^2$ is Ser (S) or Asp (D), $X^3$ is Val (V), $X^4$ is Leu (L), $X^5$ is Ser (S), and $X^6$ is Leu (L). In certain embodiments, $X^1$ is Val (V), $X^2$ is Asp (D), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                                           (SEQ ID NO: 11)
Leu-Pro-Val-Asp-Met-Val-Leu-Ile-Ser-Leu.
```

In certain embodiments, $X^1$ is Val (V), $X^2$ is Ser (S), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                              (SEQ ID NO: 12)
Leu-Pro-Val-Ser-Met-Val-Leu-Ile-Ser-Leu.
```

In certain embodiments, $X^1$ is Val (V), $X^2$ is Ser (S), $X^3$ is Gly (G), $X^4$ is Leu (L), $X^5$ is Ser (S), and $X^6$ is Val (V). In such embodiments, the peptide comprises a contiguous stretch of amino acids having the consensus amino acid sequence:

```
                              (SEQ ID NO: 13)
Leu-Pro-Val-Ser-Met-Gly-Leu-Ile-Ser-Val.
```

In certain embodiments, $X^1$ is Val (V), $X^2$ is Ser (S), $X^3$ is Ile (I), $X^4$ is Ile (I), $X^5$ is Met (M), and $X^6$ is Leu (L). In such embodiments, the peptide comprises a contiguous stretch of amino acids having the consensus amino acid sequence:

```
                              (SEQ ID NO: 14)
Leu-Pro-Val-Ser-Met-Ile-Ile-Ile-Met-Leu.
```

In certain embodiments, $X^1$ is Ile (I), $X^2$ is Ser (S), $X^3$ is Gly (G), $X^4$ is Leu (L), $X^5$ is Ser (S), and $X^6$ is Ala (A). In such embodiments, the peptide comprises a contiguous stretch of amino acids having the consensus amino acid sequence:

```
                              (SEQ ID NO: 15)
Leu-Pro-Ile-Ser-Met-Gly-Leu-Ile-Ser-Ala.
```

Examples of suitable embodiments include where: $X^1$ is Val and $X^2$ is Ser, $X^1$ is Val and $X^2$ is Asp, $X^1$ is Val and $X^3$ is Val, $X^1$ is Val and $X^3$ is Gly, $X^1$ is Val and $X^3$ is Ile, $X^1$ is Val and $X^4$ is Leu, $X^1$ is Val and $X^4$ is Ile, $X^1$ is Val and $X^5$ is Ser, $X^1$ is Val and $X^5$ is Met, $X^1$ is Val and $X^6$ is Leu, $X^1$ is Val and $X^6$ is Val, $X^1$ is Val and $X^6$ is Ala, $X^1$ is Ile and $X^2$ is Ser, $X^1$ is Ile and $X^2$ is Asp, $X^1$ is Ile and $X^3$ is Val, $X^1$ is Ile and $X^3$ is Gly, $X^1$ is Ile and $X^3$ is Ile, $X^1$ is Ile and $X^4$ is Leu, $X^1$ is Ile and $X^4$ is Ile, $X^1$ is Ile and $X^5$ is Ser, $X^1$ is Ile and $X^5$ is Met, $X^1$ is Ile and $X^6$ is Leu, $X^1$ is Ile and $X^6$ is Val, $X^1$ is Ile and $X^6$ is Ala, $X^2$ is Ser and $X^3$ is Val, $X^2$ is Ser and $X^3$ is Gly, $X^2$ is Ser and $X^3$ is Ile, $X^2$ is Ser and $X^4$ is Leu, $X^2$ is Ser and $X^4$ is Ile, $X^2$ is Ser and $X^5$ is Ser, $X^2$ is Ser and $X^5$ is Met, $X^2$ is Ser and $X^6$ is Leu, $X^2$ is Ser and $X^6$ is Val, $X^2$ is Ser and $X^6$ is Ala, $X^2$ is Asp and $X^3$ is Val, $X^2$ is Asp and $X^3$ is Gly, $X^2$ is Asp and $X^3$ is Ile, $X^2$ is Asp and $X^4$ is Leu, $X^2$ is Asp and $X^4$ is Ile, $X^2$ is Asp and $X^5$ is Ser, $X^2$ is Asp and $X^5$ is Met, $X^2$ is Asp and $X^6$ is Leu, $X^2$ is Asp and $X^6$ is Val, $X^2$ is Asp and $X^6$ is Ala, $X^3$ is Val and $X^4$ is Leu, $X^3$ is Val and $X^4$ is Ile, $X^3$ is Val and $X^5$ is Ser, $X^3$ is Val and $X^5$ is Met, $X^3$ is Val and $X^6$ is Leu, $X^3$ is Val and $X^6$ is Val, $X^3$ is Val and $X^6$ is Ala, $X^3$ is Gly and $X^4$ is Leu, $X^3$ is Gly and $X^4$ is Ile, $X^3$ is Gly and $X^5$ is Ser, $X^3$ is Gly and $X^5$ is Met, $X^3$ is Gly and $X^6$ is Leu, $X^3$ is Gly and $X^6$ is Val, $X^3$ is Gly and $X^6$ is Ala, $X^3$ is Ile and $X^4$ is Leu, $X^3$ is Ile and $X^4$ is Ile, $X^3$ is Ile and $X^5$ is Ser, $X^3$ is Ile and $X^5$ is Met, $X^3$ is Ile and $X^6$ is Leu, $X^3$ is Ile and $X^6$ is Val, $X^3$ is Ile and $X^6$ is Ala, $X^4$ is Leu and $X^5$ is Ser, $X^4$ is Leu and $X^5$ is Met, $X^4$ is Leu and $X^6$ is Leu, $X^4$ is Leu and $X^6$ is Val, $X^4$ is Leu and $X^6$ is Ala, $X^4$ is Ile and $X^5$ is Ser, $X^4$ is Ile and $X^5$ is Met, $X^4$ is Ile and $X^6$ is Leu, $X^4$ is Ile and $X^6$ is Val, $X^4$ is Ile and $X^6$ is Ala, $X^5$ is Ser and $X^6$ is Leu, $X^5$ is Ser and $X^6$ is Val, $X^5$ is Ser and $X^6$ is Ala, $X^5$ is Met and $X^6$ is Leu, $X^5$ is Met and $X^6$ is Val, and $X^5$ is Met and $X^6$ is Ala.

In certain embodiments, the AQP-4 peptide may comprise a contiguous stretch of amino acids having the consensus amino acid sequence:

Leu-Pro-Val-X-Met-Val-Leu-Ile-Ser-Leu (Formula II)

wherein X is any amino acid (SEQ ID NO:17).

In some such embodiments, X is Ser (S) or Asp (D). As such, in some embodiments, X is Ser (S) and the peptide comprises a contiguous stretch of amino acids having the consensus amino acid sequence: LPVSMVLISL (SEQ ID NO:12). In some embodiments, X is Asp (D) and the peptide comprises a contiguous stretch of amino acids having the consensus amino acid sequence: LPVDMVLISL (SEQ ID NO:11).

In certain embodiments, the peptide may comprise an amino acid sequence having at least 50%, at least 60%, at least 70%, at least 80%, or at least 90% sequence identity to a contiguous stretch of amino acids in the sequence of AQP-4 peptide p63-76 (EKPLPVDMVLISLC, SEQ ID NO:7), wherein the peptide is up to 50 amino acids in length. As used herein, p63-76 in the context of AQP-4 peptide refers to a peptide having the amino acids sequence of amino acid starting at position 63 and ending at position 76 of human AQP-4 protein sequence shown in FIG. 6.

In certain embodiments, the peptide may include a contiguous stretch of ten amino acids having at least 50%, at least 60%, at least 70%, at least 80%, or at least 90% sequence identity to a contiguous stretch of ten amino acids in the sequence of AQP-4 peptide p63-76. In certain embodiments, the peptide may include a contiguous stretch of ten amino acids having at least 70%, or at least 80% sequence identity to a contiguous stretch of ten amino acids of AQP-4 peptide p63-76. In certain embodiments, the peptide may include a contiguous stretch of ten amino acids having at least 90% sequence identity to a contiguous stretch of ten amino acids of AQP-4 peptide p63-76.

In certain embodiments, the peptide may include a contiguous stretch of ten amino acids having at least 70% sequence identity to the amino acid sequence of AQP-4 peptide p66-75 (LPVDMVLISL, SEQ ID NO:11). In certain embodiments, the peptide may include a contiguous stretch of ten amino acids having at least 80% sequence identity to the amino acid sequence of AQP-4 peptide p66-75. In certain embodiments, the peptide may include a contiguous stretch of ten amino acids having at least 90% sequence identity to the amino acid sequence of AQP-4 peptide p66-75. As used herein, p66-75 in the context of AQP-4 peptide refers to a peptide having the amino acids sequence of amino acid starting at position 66 and ending at position 75 of human AQP-4 protein sequence shown in FIG. 6.

In certain embodiments, the peptide may be AQP-4 peptide including the AQP-4 p61-80 sequence. In certain embodiments, the peptide may be AQP-4 p61-80 peptide. As used herein, p61-80 in the context of AQP-4 peptide refers to a peptide having the amino acids sequence of amino acid starting at position 61 and ending at position 80 of human AQP-4 protein sequence shown in FIG. 6. In certain embodiments, the peptide may be AQP-4 p63-76 peptide. In certain embodiments, the peptide may be AQP-4 p66-75 peptide (LPVDMVLISL, SEQ ID NO:11).

In certain embodiments, the peptide may be derived from ABC transporter permease (ABC-TP) protein of a *Clostridium* species. In certain cases, the peptide may be a peptide derived from ABC-TP protein from a strain of bacterium in the genus *Clostridium* (e.g., *Clostridium perfringens, Clostridium scindens, Clostridium sporogens, Clostridium hylemonae*, and the like). For example, in certain cases, the peptide may be a peptide derived from ABC-TP protein having the accession no. ZP_02952885.1, ZP_02638213.1, ZP_02634520.1, ZP_02630305.1, ZP_02431563, ZP_02995934, or ZP_03776873.1). In certain cases, the peptide may include a sequence of ABC-TP protein derived peptide p204-217 (FIILPVSMVLISLV, SEQ ID NO:8). As used herein, p204-217 in the context of AQP-4 peptide refers to a peptide having the amino acids sequence of amino acid starting at position 204 and ending at position 217 of protein sequence shown in FIG. 7. In certain cases, the peptide may include a sequence of ABC-TP protein derived peptide p207-216 (LPVSMVLISL, SEQ ID NO:12). As used herein, p207-216 in the context of AQP-4 peptide refers to a peptide having the amino acids sequence of amino acid starting at position 207 and ending at position 216 of protein sequence shown in FIG. 7. In certain cases, the peptide may be ABC-TP protein derived peptide p204-217 (FIILPVSMVLISLV, SEQ ID NO:8). In certain cases, the peptide may be ABC-TP protein derived peptide p207-216 (LPVSMVLISL, SEQ ID NO:12). In other cases, the peptide may be derived from the expressed or predicted ABC-TP protein in *Clostridium* species, including commensal bacteria *C. scindens* and *C. hylemonae* as well as the pathogenic strain *C. sporogenes*.

In certain embodiments, the peptide may be 5-50 amino acids long, such as, 5-40 amino acids long, or 5-30 amino acids long, or 5-25 amino acids long, or 5-20 amino acids long, or 5-15 amino acids long, or 10-20 amino acids long, or 10-15 amino acids long. For example, the peptide may be 5 amino acids long, or 7 amino acids long, or 10 amino acids long, or 15 amino acids long, or 20 amino acids long, or 25 amino acids long, or 30 amino acids long, or 35 amino acids long, or 40 amino acids long, or 45 amino acids long, or 50 amino acids long.

In certain embodiments, the peptide may be a peptide up to 50 amino acids in length (for example, up to 40 amino acids long, 30 amino acids long, such as 10-20 amino acids long, or 10-15 amino acids long) and including a contiguous stretch of amino acids having: (i) the sequence of p66-75 (LPVDMVLISL, SEQ ID NO:11) or (ii) a sequence at least 90% identical to the amino acid sequence LPVDMVLISL (SEQ ID NO:11).

In certain embodiments, the peptide may be a peptide up to 50 amino acids in length (for example, up to 40 amino acids long, 30 amino acids long, such as 10-20 amino acids long, or 10-15 amino acids long) and including a contiguous stretch of amino acids having: (i) the sequence of p66-75 (LPVDMVLISL, SEQ ID NO:11), or (ii) the sequence of p207-216 (LPVSMVLISL, SEQ ID NO:12), (iii) or the sequence of p156-170 (AGHGLLVELIITFQL, SEQ ID NO:5), (iv) or the sequence of p261-280 (RFKEAFSKAAQQTKGSYMEV, SEQ ID NO:6).

In certain cases, the peptides may include amino acid substitutions compared to the sequence of p61-80. In certain embodiments, these amino acid substitutions may be conservative substitutions. By conservative substitutions is intended substitution of an amino acid with a similar amino acid, such as those from the following groups: 1) gly, ala; 2) val, ile, leu; asp, glu; 3) asn, gln; 4) ser, thr; 5) lys, arg; and 6) phe, tyr. In certain embodiments, the amino acids substitutions may be guided by the amino acid sequence in AQP-4 protein, predicted AQP-4 protein, or AQP-4 like proteins in other species, such as, mouse, rat, hamster, non-human primates, and macaques. In certain embodiments, the amino acids substitutions may be guided by the amino acid sequence in ABC-TP protein or predicted ABC-TP protein of *Clostridium* species, such as, *Clostridium perfringens*, *C. scindens*, *C. hylemonae*, and *C. sporogenes*, for example. Predicted AQP-4 proteins or ABC-TP proteins can be identified by using methods known in the art, such as, by performing sequence search using Basic Local Alignment Search Tool (BLAST) with the amino acid sequence of full length or partial AQP-4 or ABC-TP protein.

In certain cases, the peptide may be an AQP-4 peptide comprising a contiguous stretch of amino acids of peptide p131-150 having the sequence:

GILYLVTPPSVVGGLGVTMV    (SEQ ID NO: 3)

wherein the peptide is up to 50 amino acids in length.

In certain cases, the peptide may be an AQP-4 peptide comprising a contiguous stretch of amino acids of peptide p211-230 having the sequence:

SMNPARSFGPAVIMGNWENH    (SEQ ID NO: 4)

wherein the peptide is up to 50 amino acids in length.

In certain cases, the peptide may be an AQP-4 peptide comprising a contiguous stretch of amino acids of peptide p156-170 having the sequence:

(AGHGLLVELIITFQL, SEQ ID NO: 5), wherein the peptide is up to 50 amino acids in length.

In certain cases, the peptide may be an AQP-4 peptide comprising a contiguous stretch of amino acids of peptide p261-280 having the sequence:

(RFKEAFSKAAQQTKGSYMEV, SEQ ID NO: 6), wherein the peptide is up to 50 amino acids in length.

The peptides disclosed herein may be modified covalently or non-covalently to increase stability of the peptides, such as, increase in vivo half-life, increase bioavailability, or for additional functionality. For example, the peptides may include non-natural amino acids, modifications of the natural amino acids, covalent attachment of a tag, such as, avidin or biotin, or the like.

Also disclosed herein are compositions comprising the peptide(s) provided herein. The composition may include one or more peptide as set forth above. In certain cases, the composition may include a mixture of a plurality of peptides set forth the above, such as, 2, 3, 4, 5, 6, 10, 12, 15, 20, or more peptides. The composition may be in solid, semi-solid, liquid or gaseous form, such as, powders, granules, solutions, injections, inhalants, gels, hydrogels, microspheres, etc. In certain cases, the peptide composition may include a diluent, buffer, or other components, such as, water, buffered water, physiological saline, Phosphate Buffered Saline (PBS), Ringer's solution, dextrose solution, and Hank's solution.

In certain cases, a composition comprising a peptide(s) as disclosed above, may be a pharmaceutical composition. Pharmaceutical compositions can include, depending on the formulation desired, pharmaceutically-acceptable, non-toxic carriers or diluents, which are commonly used to formulate pharmaceutical compositions for animal or human administration. The diluent or carrier is selected so as not to affect the biological activity of the combination. Examples of such diluents or carriers are distilled water, buffered water, physiological saline, Phosphate Buffered Saline (PBS), Ringer's solution, dextrose solution, and Hank's solution. In certain embodiments, the pharmaceutical composition or formulation can include other carriers, or other diluents, or adjuvants, or non-toxic, nontherapeutic, nonimmunogenic stabilizers, or excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant. In certain cases, the peptide can be complexed with various well-known compounds that enhance the in vivo stability of the peptide, or otherwise enhance its pharmacological properties (e.g., increase the half-life of the peptide, reduce its toxicity, enhance solubility or uptake). Examples of such modifications or complexing agents include sulfate, gluconate, citrate and phosphate. The peptides of the composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process.

Diagnosis of NMO

As shown herein, AQP4-specific T cells are present in patient with NMO. Accordingly, the peptides disclosed herein may be used to diagnose NMO in a subject.

In general, a method for diagnosing NMO in a subject comprises contacting a sample from the subject with a peptide comprising a contiguous stretch of amino acids having the consensus amino acid sequence:

$$\text{Leu-Pro-}X^1\text{-}X^2\text{-Met-}X^3\text{-}X^4\text{-Ile-}X^5\text{-}X^6 \quad \text{(Formula I)}$$

wherein $X^1$, $X^2$, $X^3$, $X^4$, $X^5$, and $X^6$ are any amino acid (SEQ ID NO:16), and wherein the peptide is up to 50 amino acids in length.

In certain embodiments, $X^1$ is Val (V) or Ile (I). In certain embodiments, $X^2$ is Ser (S) or Asp (D). In certain embodiments, $X^3$ is Val (V), Ile (I), or Gly (G). In certain embodiments, $X^4$ is Leu (L) or Ile (I). In certain embodiments, $X^5$ is Met (M) or Ser (S). In certain embodiments, $X^6$ is Leu (L), Val (V), or Ala (A). In certain embodiments, $X^1$ is Val (V), $X^2$ is Ser (S) or Asp (D), $X^3$ is Val (V), $X^4$ is Leu (L), $X^5$ is Ser (S), and $X^6$ is Leu (L). In certain embodiments, $X^1$ is Val (V), $X^2$ is Asp (D), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                                        (SEQ ID NO: 11)
Leu-Pro-Val-Asp-Met-Val-Leu-Ile-Ser-Leu.
```

In certain embodiments, $X^1$ is Val (V), $X^2$ is Ser (S), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                                        (SEQ ID NO: 12)
Leu-Pro-Val-Ser-Met-Val-Leu-Ile-Ser-Leu.
```

In certain embodiments, $X^1$ is Val (V), $X^2$ is Ser (S), $X^3$ is Gly (G), $X^4$ is Leu (L), $X^5$ is Ser (S), and $X^6$ is Val (V). In such embodiments, the peptide comprises a contiguous stretch of amino acids having the consensus amino acid sequence:

```
                                        (SEQ ID NO: 13)
Leu-Pro-Val-Ser-Met-Gly-Leu-Ile-Ser-Val.
```

In certain embodiments, $X^1$ is Val (V), $X^2$ is Ser (S), $X^3$ is Ile (I), $X^4$ is Ile (I), $X^5$ is Met (M), and $X^6$ is Leu (L). In such embodiments, the peptide comprises a contiguous stretch of amino acids having the consensus amino acid sequence:

```
                                        (SEQ ID NO: 14)
Leu-Pro-Val-Ser-Met-Ile-Ile-Ile-Met-Leu.
```

In certain embodiments, $X^1$ is Ile (I), $X^2$ is Ser (S), $X^3$ is Gly (G), $X^4$ is Leu (L), $X^5$ is Ser (S), and $X^6$ is Ala (A). In such embodiments, the peptide comprises a contiguous stretch of amino acids having the consensus amino acid sequence:

```
                                        (SEQ ID NO: 15)
Leu-Pro-Ile-Ser-Met-Gly-Leu-Ile-Ser-Ala.
```

Examples of suitable embodiments include where: $X^1$ is Val and $X^2$ is Ser, $X^1$ is Val and $X^2$ is Asp, $X^1$ is Val and $X^3$ is Val, $X^1$ is Val and $X^3$ is Gly, $X^1$ is Val and $X^3$ is Ile, $X^1$ is Val and $X^4$ is Leu, $X^1$ is Val and $X^4$ is Ile, $X^1$ is Val and $X^5$ is Ser, $X^1$ is Val and $X^5$ is Met, $X^1$ is Val and $X^6$ is Leu, $X^1$ is Val and $X^6$ is Val, $X^1$ is Val and $X^6$ is Ala, $X^1$ is Ile and $X^2$ is Ser, $X^1$ is Ile and $X^2$ is Asp, $X^1$ is Ile and $X^3$ is Val, $X^1$ is Ile and $X^3$ is Gly, $X^1$ is Ile and $X^3$ is Ile, $X^1$ is Ile and $X^4$ is Leu, $X^1$ is Ile and $X^4$ is Ile, $X^1$ is Ile and $X^5$ is Ser, $X^1$ is Ile and $X^5$ is Met, $X^1$ is Ile and $X^6$ is Leu, $X^1$ is Ile and $X^6$ is Val, $X^1$ is Ile and $X^6$ is Ala, $X^2$ is Ser and $X^3$ is Val, $X^2$ is Ser and $X^3$ is Gly, $X^2$ is Ser and $X^3$ is Ile, $X^2$ is Ser and $X^4$ is Leu, $X^2$ is Ser and $X^4$ is Ile, $X^2$ is Ser and $X^5$ is Ser, $X^2$ is Ser and $X^5$ is Met, $X^2$ is Ser and $X^6$ is Leu, $X^2$ is Ser and $X^6$ is Val, $X^2$ is Ser and $X^6$ is Ala, $X^2$ is Asp and $X^3$ is Val, $X^2$ is Asp and $X^3$ is Gly, $X^2$ is Asp and $X^3$ is Ile, $X^2$ is Asp and $X^4$ is Leu, $X^2$ is Asp and $X^4$ is Ile, $X^2$ is Asp and $X^5$ is Ser, $X^2$ is Asp and $X^5$ is Met, $X^2$ is Asp and $X^6$ is Leu, $X^2$ is Asp and $X^6$ is Val, $X^2$ is Asp and $X^6$ is Ala, $X^3$ is Val and $X^4$ is Leu, $X^3$ is Val and $X^4$ is Ile, $X^3$ is Val and $X^5$ is Ser, $X^3$ is Val and $X^5$ is Met, $X^3$ is Val and $X^6$ is Leu, $X^3$ is Val and $X^6$ is Val, $X^3$ is Val and $X^6$ is Ala, $X^3$ is Gly and $X^4$ is Leu, $X^3$ is Gly and $X^4$ is Ile, $X^3$ is Gly and $X^5$ is Ser, $X^3$ is Gly and $X^5$ is Met, $X^3$ is Gly and $X^6$ is Leu, $X^3$ is Gly and $X^6$ is Val, $X^3$ is Gly and $X^6$ is Ala, $X^3$ is Ile and $X^4$ is Leu, $X^3$ is Ile and $X^4$ is Ile, $X^3$ is Ile and $X^5$ is Ser, $X^3$ is Ile and $X^5$ is Met, $X^3$ is Ile and $X^6$ is Leu, $X^3$ is Ile and $X^6$ is Val, $X^3$ is Ile and $X^6$ is Ala, $X^4$ is Leu and $X^5$ is Ser, $X^4$ is Leu and $X^5$ is Met, $X^4$ is Leu and $X^6$ is Leu, $X^4$ is Leu and $X^6$ is Val, $X^4$ is Leu and $X^6$ is Ala, $X^4$ is Ile and $X^5$ is Ser, $X^4$ is Ile and $X^5$ is Met, $X^4$ is Ile and $X^6$ is Leu, $X^4$ is Ile and $X^6$ is Val, $X^4$ is Ile and $X^6$ is Ala, $X^5$ is Ser and $X^6$ is Leu, $X^5$ is Ser and $X^6$ is Val, $X^5$ is Ser and $X^6$ is Ala, $X^5$ is Met and $X^6$ is Leu, $X^5$ is Met and $X^6$ is Val, and $X^5$ is Met and $X^6$ is Ala.

In certain embodiments, the peptide may comprise a contiguous stretch of amino acids having the consensus amino acid sequence:

$$\text{Leu-Pro-Val-X-Met-Val-Leu-Ile-Ser-Leu} \quad \text{(Formula II)}$$

wherein X is any amino acid (SEQ ID NO:17).

In some such embodiments, X is Ser (S) or Asp (D). As such, in some embodiments, X is Ser (S) and the peptide comprises a contiguous stretch of amino acids having the consensus amino acid sequence: LPVSMVLISL (SEQ ID NO:12). In some embodiments, X is Asp (D) and the peptide comprises a contiguous stretch of amino acids having the consensus amino acid sequence: LPVDMVLISL (SEQ ID NO:11).

In certain cases, the method comprises contacting a sample from the subject with a peptide comprising an amino acid sequence having at least 60% sequence identity to the amino acid sequence of a human Aquaphorin-4 (AQP-4) peptide: LPVDMVLISL (SEQ ID NO:11), wherein the peptide is up to 50 amino acids in length, wherein the sample comprises T cells; and measuring the number of T cells, wherein an increase in the number of T cells as compared to a control indicates that the subject has NMO.

In certain cases, the subject may be exhibiting symptoms of NMO. In other cases, the subject may be asymptomatic but may be predisposed to NMO. In certain embodiments, the subject may have symptoms that are common to NMO and other diseases, such as, multiple sclerosis. In certain cases, the subject may be at an early stage of the disease before all clinical criteria of NMO are evident. In certain cases, the subject may exhibit optic neuritis, myelitis, and at least two of three supportive criteria: (i) MRI evidence of a contiguous spinal cord lesion 3 or more segments in length, (ii) onset brain MRI nondiagnostic for multiple sclerosis, and (iii) NMO-IgG seropositivity. CNS involvement beyond the optic nerves and spinal cord is compatible with NMO (Wingerchuk et al. (2006) Neurology, May 23; 66(10):1485-9)

In certain embodiments, the sample may be a body fluid sample, such as, blood, serum, plasma, cerebrospinal fluid. In certain cases, the sample may be a sample containing Peripheral blood mononuclear cells (PBMC) isolated from the subject. In other cases, the sample may be a sample containing T cells isolated from the subject. In certain cases, the sample may be a solid tissue sample, such as, biopsy sample, for example, sample obtained from brain biopsy, spinal cord biopsy, and the like.

The contacting may be carried out for a period of time sufficient to detect proliferation of T cells. In certain cases, the contacting may be carried out for a period of 1 day to 30 days, such as, 1 day, or 5 days, or 10 days, or 15 days, or 20 days, or 25 days, or 30 days.

An increase in T cell proliferation of at least about 5%, or at least about 10%, or at least about 20%, or at least about 50%, or at least about 70%, or at least about 80%, or at least about 90%, or more, compared to a negative control may indicate that the subject has NMO.

Any suitable negative control may be used for comparison. Suitable negative controls include samples obtained from healthy controls, sample from the subject being diagnosed, where the sample is not contacted with the peptide, for example.

In certain embodiments, T cell proliferation may be compared to a threshold value or range. For example, a normal threshold value or range of T cell proliferation may be determined by contacting the peptides disclosed herein with samples from healthy controls. An increase in T cell proliferation of at least about 5%, or at least about 10%, or at least about 20%, or at least about 50%, or at least about 70%, or at least about 80%, or at least about 90%, or more, compared to the normal threshold value or range may indicate that the subject has NMO.

T cell proliferation may be measured by methods known in the art, such as, the methods disclosed herein.

In certain embodiments, the T cell measured in the method may be a CD4+ T cell. In certain cases, the T cell measured in the method may be a Th17 T cell.

Methods of Screening

A method for screening for candidate agents for inhibiting proliferation of T cells in response to exposure to a peptide disclosed herein is also provided. As shown herein, T cells from NMO patients proliferate when exposed to a peptide comprising an amino acid sequence having at least 60% sequence identity to the amino acid sequence of a human Aquaphorin-4 (AQP-4) peptide LPVDMVLISL (SEQ ID NO:11). Moreover, an increased frequency of these T cells are Th17 cells which may lead to NMO pathogenesis. Accordingly, the identification of agents that may inhibit the AQP-4 peptide or peptide homologous to AQP-4 peptide mediated proliferation of T cells may be useful in treating NMO.

In general, the method for screening for inhibitors of proliferation of T cells comprises contacting a sample from the subject with: (i) a peptide comprising a contiguous stretch of amino acids having the consensus amino acid sequence:

$$\text{Leu-Pro-}X^1\text{-}X^2\text{-Met-}X^3\text{-}X^4\text{-Ile-}X^5\text{-}X^6 \qquad \text{(Formula I)}$$

wherein $X^1$, $X^2$, $X^3$, $X^4$, $X^5$, and $X^6$ are any amino acid (SEQ ID NO:16), and wherein the peptide is up to 50 amino acids in length; and (ii) a candidate agent and evaluating the number of T cells, wherein a decrease in the number of T cells as compared to a control indicates that the candidate agent inhibits proliferation of T cells. In certain embodiments, $X^1$ is Val (V) or Ile (I). In certain embodiments, $X^2$ is Ser (S) or Asp (D). In certain embodiments, $X^3$ is Val (V), Ile (I), or Gly (G). In certain embodiments, $X^4$ is Leu (L) or Ile (I). In certain embodiments, $X^5$ is Met (M) or Ser (S). In certain embodiments, $X^6$ is Leu (L), Val (V), or Ala (A). In certain embodiments, $X^1$ is Val (V), $X^2$ is Ser (S) or Asp (D), $X^3$ is Val (V), $X^4$ is Leu (L), $X^5$ is Ser (S), and $X^6$ is Leu (L).

In certain embodiments, $X^1$ is Val (V), $X^2$ is Asp (D), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                                         (SEQ ID NO: 11)
     Leu-Pro-Val-Asp-Met-Val-Leu-Ile-Ser-Leu.
```

In certain embodiments, $X^1$ is Val (V), $X^2$ is Ser (S), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                                         (SEQ ID NO: 12)
     Leu-Pro-Val-Ser-Met-Val-Leu-Ile-Ser-Leu.
```

In certain embodiments, $X^1$ is Val (V), $X^2$ is Ser (S), $X^3$ is Gly (G), $X^4$ is Leu (L), $X^5$ is Ser (S), and $X^6$ is Val (V). In such embodiments, the peptide comprises a contiguous stretch of amino acids having the consensus amino acid sequence:

```
                                         (SEQ ID NO: 13)
     Leu-Pro-Val-Ser-Met-Gly-Leu-Ile-Ser-Val.
```

In certain embodiments, $X^1$ is Val (V), $X^2$ is Ser (S), $X^3$ is Ile (I), $X^4$ is Ile (I), $X^5$ is Met (M), and $X^6$ is Leu (L). In such embodiments, the peptide comprises a contiguous stretch of amino acids having the consensus amino acid sequence:

Leu-Pro-Val-Ser-Met-Ile-Ile-Ile-Met-Leu. (SEQ ID NO: 14)

In certain embodiments, $X^1$ is Ile (I), $X^2$ is Ser (S), $X^3$ is Gly (G), $X^4$ is Leu (L), $X^5$ is Ser (S), and $X^6$ is Ala (A). In such embodiments, the peptide comprises a contiguous stretch of amino acids having the consensus amino acid sequence:

Leu-Pro-Ile-Ser-Met-Gly-Leu-Ile-Ser-Ala. (SEQ ID NO: 15)

Examples of suitable embodiments include where: $X^1$ is Val and $X^2$ is Ser, $X^1$ is Val and $X^2$ is Asp, $X^1$ is Val and $X^3$ is Val, $X^1$ is Val and $X^3$ is Gly, $X^1$ is Val and $X^3$ is Ile, $X^1$ is Val and $X^4$ is Leu, $X^1$ is Val and $X^4$ is Ile, $X^1$ is Val and $X^5$ is Ser, $X^1$ is Val and $X^5$ is Met, $X^1$ is Val and $X^6$ is Leu, $X^1$ is Val and $X^6$ is Val, $X^1$ is Val and $X^6$ is Ala, $X^1$ is Ile and $X^2$ is Ser, $X^1$ is Ile and $X^2$ is Asp, $X^1$ is Ile and $X^3$ is Val, $X^1$ is Ile and $X^3$ is Gly, $X^1$ is Ile and $X^3$ is Ile, $X^1$ is Ile and $X^4$ is Leu, $X^1$ is Ile and $X^4$ is Ile, $X^1$ is Ile and $X^5$ is Ser, $X^1$ is Ile and $X^5$ is Met, $X^1$ is Ile and $X^6$ is Leu, $X^1$ is Ile and $X^6$ is Val, $X^1$ is Ile and $X^6$ is Ala, $X^2$ is Ser and $X^3$ is Val, $X^2$ is Ser and $X^3$ is Gly, $X^2$ is Ser and $X^3$ is Ile, $X^2$ is Ser and $X^4$ is Leu, $X^2$ is Ser and $X^4$ is Ile, $X^2$ is Ser and $X^5$ is Ser, $X^2$ is Ser and $X^5$ is Met, $X^2$ is Ser and $X^6$ is Leu, $X^2$ is Ser and $X^6$ is Val, $X^2$ is Ser and $X^6$ is Ala, $X^2$ is Asp and $X^3$ is Val, $X^2$ is Asp and $X^3$ is Gly, $X^2$ is Asp and $X^3$ is Ile, $X^2$ is Asp and $X^4$ is Leu, $X^2$ is Asp and $X^4$ is Ile, $X^2$ is Asp and $X^5$ is Ser, $X^2$ is Asp and $X^5$ is Met, $X^2$ is Asp and $X^6$ is Leu, $X^2$ is Asp and $X^6$ is Val, $X^2$ is Asp and $X^6$ is Ala, $X^3$ is Val and $X^4$ is Leu, $X^3$ is Val and $X^4$ is Ile, $X^3$ is Val and $X^5$ is Ser, $X^3$ is Val and $X^5$ is Met, $X^3$ is Val and $X^6$ is Leu, $X^3$ is Val and $X^6$ is Val, $X^3$ is Val and $X^6$ is Ala, $X^3$ is Gly and $X^4$ is Leu, $X^3$ is Gly and $X^4$ is Ile, $X^3$ is Gly and $X^5$ is Ser, $X^3$ is Gly and $X^5$ is Met, $X^3$ is Gly and $X^6$ is Leu, $X^3$ is Gly and $X^6$ is Val, $X^3$ is Gly and $X^6$ is Ala, $X^3$ is Ile and $X^4$ is Leu, $X^3$ is Ile and $X^4$ is Ile, $X^3$ is Ile and $X^5$ is Ser, $X^3$ is Ile and $X^5$ is Met, $X^3$ is Ile and $X^6$ is Leu, $X^3$ is Ile and $X^6$ is Val, $X^3$ is Ile and $X^6$ is Ala, $X^4$ is Leu and $X^5$ is Ser, $X^4$ is Leu and $X^5$ is Met, $X^4$ is Leu and $X^6$ is Leu, $X^4$ is Leu and $X^6$ is Val, $X^4$ is Leu and $X^6$ is Ala, $X^4$ is Ile and $X^5$ is Ser, $X^4$ is Ile and $X^5$ is Met, $X^4$ is Ile and $X^6$ is Leu, $X^4$ is Ile and $X^6$ is Val, $X^4$ is Ile and $X^6$ is Ala, $X^5$ is Ser and $X^6$ is Leu, $X^5$ is Ser and $X^6$ is Val, $X^5$ is Ser and $X^6$ is Ala, $X^5$ is Met and $X^6$ is Leu, $X^5$ is Met and $X^6$ is Val, and $X^5$ is Met and $X^6$ is Ala.

In certain embodiments, the peptide may comprise a contiguous stretch of amino acids having the consensus amino acid sequence:

Leu-Pro-Val-X-Met-Val-Leu-Ile-Ser-Leu   (Formula II)

wherein X is any amino acid (SEQ ID NO:17).

In some such embodiments, X is Ser (S) or Asp (D). As such, in some embodiments, X is Ser (S) and the peptide comprises a contiguous stretch of amino acids having the consensus amino acid sequence: LPVSMVLISL (SEQ ID NO:12). In some embodiments, X is Asp (D) and the peptide comprises a contiguous stretch of amino acids having the consensus amino acid sequence: LPVDMVLISL (SEQ ID NO:11).

In certain cases, the method may comprise contacting a T cell obtained from a subject having Neuromyelitis Optica with (i) a peptide comprising an amino acid sequence having at least 60% sequence identity to the amino acid sequence of a human Aquaphorin-4 (AQP-4) peptide: LPVDMVLISL (SEQ ID NO:11) wherein the peptide is up to 50 amino acids in length, and (ii) a candidate agent and evaluating the number of T cells, wherein a decrease in the number of T cells as compared to a control indicates that the candidate agent inhibits proliferation of T cells.

Candidate agents of interest for screening include biologically active agents of numerous chemical classes, organic molecules, inorganic molecules, organometallic molecules, immunoglobulins, peptides, proteins, genetic sequences, etc. Also of interest are small organic molecules, which comprise functional groups necessary for structural interaction with proteins, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Candidate agents may be compounds. Compounds may be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs.

A plurality of assays may be run in parallel with different concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in binding.

A candidate agent is identified as an inhibitor of AQP-4 specific T cell proliferation if it decreases AQP-4 specific T cell proliferation by at least about 5%, or at least about 10%, or at least about 20%, or at least about 50%, or at least about 70%, or at least about 80%, or at least about 90%, or more, compared to AQP-4 specific T cell proliferation in absence of the candidate agent, or another negative control.

A T cell obtained from a NMO patient used in the screening method, may be present in a blood sample from the NMO patient, or present in a purified form, such as, isolated from the blood sample. The contacting with a peptide as provided herein and a candidate agent may be simultaneous or sequential. The contacting may be performed for 1 day, or 5 days, or 10 days, or 15 days, or 20 days, or 25 days, or 30 days. T cell proliferation may be evaluated by methods known in the art.

Induction of Immune Tolerance to AQP4

A method for inducing immune tolerance to AQP-4 protein and fragments thereof in a subject is also provided. As such, the peptides disclosed herein may be used in a tolerizing therapy to suppress immune response to AQP-4 protein and fragments thereof. In general, the method comprises administering an effective dose of a peptide to a subject, wherein the peptide comprises a contiguous stretch of amino acids having the consensus amino acid sequence:

Leu-Pro-X$^1$-X$^2$-Met-X$^3$-X$^4$-Ile-X$^5$-X$^6$ (Formula I)

wherein X$^1$, X$^2$, X$^3$, X$^4$, X$^5$, and X$^6$ are any amino acid (SEQ ID NO:16),
wherein the peptide is up to 50 amino acids in length, and
wherein the administering the peptide induces immune tolerance to AQP-4 protein and fragments thereof in the subject.

In certain embodiments, X$^1$ is Val (V) or Ile (I). In certain embodiments, X$^2$ is Ser (S) or Asp (D). In certain embodiments, X$^3$ is Val (V), Ile (I), or Gly (G). In certain embodiments, X$^4$ is Leu (L) or Ile (I). In certain embodiments, X$^5$ is Met (M) or Ser (S). In certain embodiments, X$^6$ is Leu (L), Val (V), or Ala (A). In certain embodiments, X$^1$ is Val (V), X$^2$ is Ser (S) or Asp (D), X$^3$ is Val (V), X$^4$ is Leu (L), X$^5$ is Ser (S), and X$^6$ is Leu (L).

In certain embodiments, X$^1$ is Val (V), X$^2$ is Asp (D), X$^3$ is Val (V), X$^4$ is Leu (L), X$^5$ is Ser (S), and X$^6$ is Leu (L). In such embodiments, the peptide comprises a contiguous stretch of amino acids having the consensus amino acid sequence:

```
                                         (SEQ ID NO: 11)
Leu-Pro-Val-Asp-Met-Val-Leu-Ile-Ser-Leu.
```

In certain embodiments, X$^1$ is Val (V), X$^2$ is Ser (S), X$^3$ is Val (V), X$^4$ is Leu (L), X$^5$ is Ser (S), and X$^6$ is Leu (L). In such embodiments, the peptide comprises a contiguous stretch of amino acids having the consensus amino acid sequence:

```
                                         (SEQ ID NO: 12)
Leu-Pro-Val-Ser-Met-Val-Leu-Ile-Ser-Leu.
```

In certain embodiments, X$^1$ is Val (V), X$^2$ is Ser (S), X$^3$ is Gly (G), X$^4$ is Leu (L), X$^5$ is Ser (S), and X$^6$ is Val (V). In such embodiments, the peptide comprises a contiguous stretch of amino acids having the consensus amino acid sequence:

```
                                         (SEQ ID NO: 13)
Leu-Pro-Val-Ser-Met-Gly-Leu-Ile-Ser-Val.
```

In certain embodiments, X$^1$ is Val (V), X$^2$ is Ser (S), X$^3$ is Ile (I), X$^4$ is Ile (I), X$^5$ is Met (M), and X$^6$ is Leu (L). In such embodiments, the peptide comprises a contiguous stretch of amino acids having the consensus amino acid sequence:

```
                                         (SEQ ID NO: 14)
Leu-Pro-Val-Ser-Met-Ile-Ile-Ile-Met-Leu.
```

In certain embodiments, X$^1$ is Ile (I), X$^2$ is Ser (S), X$^3$ is Gly (G), X$^4$ is Leu (L), X$^5$ is Ser (S), and X$^6$ is Ala (A). In such embodiments, the peptide comprises a contiguous stretch of amino acids having the consensus amino acid sequence:

```
                                         (SEQ ID NO: 15)
Leu-Pro-Ile-Ser-Met-Gly-Leu-Ile-Ser-Ala.
```

Examples of suitable embodiments include where:
X$^1$ is Val and X$^2$ is Ser, X$^1$ is Val and X$^2$ is Asp, X$^1$ is Val and X$^3$ is Val, X$^1$ is Val and X$^3$ is Gly, X$^1$ is Val and X$^3$ is Ile, X$^1$ is Val and X$^4$ is Leu, X$^1$ is Val and X$^4$ is Ile, X$^1$ is Val and X$^5$ is Ser, X$^1$ is Val and X$^5$ is Met, X$^1$ is Val and X$^6$ is Leu, X$^1$ is Val and X$^6$ is Val, X$^1$ is Val and X$^6$ is Ala, X$^1$ is Ile and X$^2$ is Ser, X$^1$ is Ile and X$^2$ is Asp, X$^1$ is Ile and X$^3$ is Val, X$^1$ is Ile and X$^3$ is Gly, X$^1$ is Ile and X$^3$ is Ile, X$^1$ is Ile and X$^4$ is Leu, X$^1$ is Ile and X$^4$ is Ile, X$^1$ is Ile and X$^5$ is Ser, X$^1$ is Ile and X$^5$ is Met, X$^1$ is Ile and X$^6$ is Leu, X$^1$ is Ile and X$^6$ is Val, X$^1$ is Ile and X$^6$ is Ala, X$^2$ is Ser and X$^3$ is Val, X$^2$ is Ser and X$^3$ is Gly, X$^2$ is Ser and X$^3$ is Ile, X$^2$ is Ser and X$^4$ is Leu, X$^2$ is Ser and X$^4$ is Ile, X$^2$ is Ser and X$^5$ is Ser, X$^2$ is Ser and X$^5$ is Met, X$^2$ is Ser and X$^6$ is Leu, X$^2$ is Ser and X$^6$ is Val, X$^2$ is Ser and X$^6$ is Ala, X$^2$ is Asp and X$^3$ is Val, X$^2$ is Asp and X$^3$ is Gly, X$^2$ is Asp and X$^3$ is Ile, X$^2$ is Asp and X$^4$ is Leu, X$^2$ is Asp and X$^4$ is Ile, X$^2$ is Asp and X$^5$ is Ser, X$^2$ is Asp and X$^5$ is Met, X$^2$ is Asp and X$^6$ is Leu, X$^2$ is Asp and X$^6$ is Val, X$^2$ is Asp and X$^6$ is Ala, X$^3$ is Val and X$^4$ is Leu, X$^3$ is Val and X$^4$ is Ile, X$^3$ is Val and X$^5$ is Ser, X$^3$ is Val and X$^5$ is Met, X$^3$ is Val and X$^6$ is Leu, X$^3$ is Val and X$^6$ is Val, X$^3$ is Val and X$^6$ is Ala, X$^3$ is Gly and X$^4$ is Leu, X$^3$ is Gly and X$^4$ is Ile, X$^3$ is Gly and X$^5$ is Ser, X$^3$ is Gly and X$^5$ is Met, X$^3$ is Gly and X$^6$ is Leu, X$^3$ is Gly and X$^6$ is Val, X$^3$ is Gly and X$^6$ is Ala, X$^3$ is Ile and X$^4$ is Leu, X$^3$ is Ile and X$^4$ is Ile, X$^3$ is Ile and X$^5$ is Ser, X$^3$ is Ile and X$^5$ is Met, X$^3$ is Ile and X$^6$ is Leu, X$^3$ is Ile and X$^6$ is Val, X$^3$ is Ile and X$^6$ is Ala, X$^4$ is Leu and X$^5$ is Ser, X$^4$ is Leu and X$^5$ is Met, X$^4$ is Leu and X$^6$ is Leu, X$^4$ is Leu and X$^6$ is Val, X$^4$ is Leu and X$^6$ is Ala, X$^4$ is Ile and X$^5$ is Ser, X$^4$ is Ile and X$^5$ is Met, X$^4$ is Ile and X$^6$ is Leu, X$^4$ is Ile and X$^6$ is Val, X$^4$ is Ile and X$^6$ is Ala, X$^5$ is Ser and X$^6$ is Leu, X$^5$ is Ser and X$^6$ is Val, X$^5$ is Ser and X$^6$ is Ala, X$^5$ is Met and X$^6$ is Leu, X$^5$ is Met and X$^6$ is Val, and X$^5$ is Met and X$^6$ is Ala.

In certain embodiments, the peptide may comprise a contiguous stretch of amino acids having the consensus amino acid sequence:

Leu-Pro-Val-X-Met-Val-Leu-Ile-Ser-Leu (Formula II)

wherein X is any amino acid (SEQ ID NO:17).

In some such embodiments, X is Ser (S) or Asp (D). As such, in some embodiments, X is Ser (S) and the peptide comprises a contiguous stretch of amino acids having the consensus amino acid sequence: LPVSMVLISL (SEQ ID NO:12). In some embodiments, X is Asp (D) and the peptide comprises a contiguous stretch of amino acids having the consensus amino acid sequence: LPVDMVLISL (SEQ ID NO:11).

In certain embodiments, the peptide may comprise an amino acid sequence having at least 60% sequence identity to the amino acid sequence of a human Aquaphorin-4 (AQP-4) peptide having the amino acid sequence: LPVDMVLISL (SEQ ID NO:11) wherein the peptide is up to 50 amino acids in length, wherein the administering the peptide induces immune tolerance to AQP-4 protein and fragments thereof in the subject. The phrase "fragments of AQP-4 protein" as used in the context of AQP4 fragments that do not induce an immune reaction in a subject treated with the peptides disclosed herein refer to AQP4 fragments comprising an amino acid sequence homologous to the amino acid sequence of the peptide used for induction of immune tolerance. For example, the AQP4 fragments may include a stretch of amino acids having: the consensus sequence Leu-Pro-Val-X-Met-Val-Leu-Ile-Ser-Leu (SEQ ID NO:17), or having at least 60% sequence identity to the sequence: LPVDMVLISL (SEQ ID NO:11).

In certain embodiments, the subject may be predisposed or at risk of developing NMO. In certain embodiments, the subject may have been diagnosed with NMO.

The peptide(s) may be administered to an individual as a pharmaceutically acceptable composition. Pharmaceutically acceptable peptide compositions for administering to an individual may include, for example, sterile aqueous or non-aqueous solutions, suspensions, and emulsions. Examples of components, such as, carriers, present in pharmaceutically acceptable peptide compositions include, without limitation, propylene glycol, polyethylene glycol, vegetable oils, and injectable organic esters. Aqueous carriers include water, alcohol, saline, and buffered solutions. Pharmaceutically acceptable carriers can also include physiologically acceptable aqueous vehicles (e.g., physiological saline or artificial cerebral-spinal fluid) or other known carriers appropriate to specific routes of administration. Additional compounds can be included with the peptide(s) described herein, such as steroids, mucolytic agents, anti-inflammatory agents, immunosuppressants, dilators, vasoconstrictors, or combinations thereof. Preservatives, flavorings, and other additives such as, for example, anti-microbials, anti-oxidants, chelating agents, inert gases, and the like may also be present.

In certain cases, the peptide(s) may be administered at an amount that is sufficient to suppress induction of an immune response to AQP4 or fragments thereof. In certain cases, the amount may be sufficient to suppress production of AQP4 specific antibodies in the subject. In certain cases, the amount may be sufficient to suppress production of AQP4 specific T cells in the subject. In certain cases, the amount may be sufficient to suppress production of AQP4 specific-T cells and antibodies in the subject. In certain embodiments, a subject receiving the AQP4 tolerizing therapy as described above, may show a 5%-90% decrease in the titer of AQP4 specific antibodies present in the subject as compared the titer of the antibodies present before the therapy. In certain embodiments, a subject receiving the AQP4 tolerizing therapy as described above, may show a 5%-90% decrease in the number of AQP4 specific T cells present in the subject as compared the number of AQP4 specific T cells present before the therapy. In certain cases, the AQP4 tolerizing therapy may result in a substantial decrease (e.g., 5%-90% decrease) in the number of Th17 cells present in the subject as compared the number present before the therapy.

In certain cases, the peptide may be administered at a high dose, such as, 0.1-10 mg/Kg, such as, 0.1 mg/Kg, 0.3 mg/Kg, 1 mg/Kg, 3 mg/Kg, or 10 mg/Kg.

In certain cases, the peptide may be administered to the *thymus* of the subject. In certain cases, the peptide may be orally administered to the subject. In certain cases, the method may include repeated administration of the peptide, such as, every 10 days, 20 days, 30 days, 3 months, 6 months, 12 months, 3 years, 6 years, 10 years, and so forth. In certain cases, the initial dose of the peptide may be higher than the dose of the peptide in subsequent administration to the subject.

Kits

Kits including the peptides described herein are disclosed. Kits may include one or more peptides comprising a contiguous stretch of amino acids having the consensus amino acid sequence:

$$\text{Leu-Pro-}X^1\text{-}X^2\text{-Met-}X^3\text{-}X^4\text{-Ile-}X^5\text{-}X^6 \quad \text{(Formula I)}$$

wherein $X^1$, $X^2$, $X^3$, $X^4$, $X^5$, and $X^6$ are any amino acid (SEQ ID NO:16), and wherein the peptide is up to 50 amino acids in length.

In certain embodiments, $X^1$ is Val (V) or Ile (I). In certain embodiments, $X^2$ is Ser (S) or Asp (D). In certain embodiments, $X^3$ is Val (V), Ile (I), or Gly (G). In certain embodiments, $X^4$ is Leu (L) or Ile (I). In certain embodiments, $X^5$ is Met (M) or Ser (S). In certain embodiments, $X^6$ is Leu (L), Val (V), or Ala (A). In certain embodiments, $X^1$ is Val (V), $X^2$ is Ser (S) or Asp (D), $X^3$ is Val (V), $X^4$ is Leu (L), $X^5$ is Ser (S), and $X^6$ is Leu (L).

In certain embodiments, $X^1$ is Val (V), $X^2$ is Asp (D), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                                        (SEQ ID NO: 11)
Leu-Pro-Val-Asp-Met-Val-Leu-Ile-Ser-Leu.
```

In certain embodiments, $X^1$ is Val (V), $X^2$ is Ser (S), $X^3$ is Val (V), $X^4$ is Leu (L), $X^5$ is Ser (S), and $X^6$ is Leu (L). In such embodiments, the peptide comprises a contiguous stretch of amino acids having the consensus amino acid sequence:

```
                                        (SEQ ID NO: 12)
Leu-Pro-Val-Ser-Met-Val-Leu-Ile-Ser-Leu.
```

In certain embodiments, $X^1$ is Val (V), $X^2$ is Ser (S), $X^3$ is Gly (G), $X^4$ is Leu (L), $X^5$ is Ser (S), and $X^6$ is Val (V). In such embodiments, the peptide comprises a contiguous stretch of amino acids having the consensus amino acid sequence:

```
                                        (SEQ ID NO: 13)
Leu-Pro-Val-Ser-Met-Gly-Leu-Ile-Ser-Val.
```

In certain embodiments, $X^1$ is Val (V), $X^2$ is Ser (S), $X^3$ is Ile (I), $X^4$ is Ile (I), $X^5$ is Met (M), and $X^6$ is Leu (L). In such embodiments, the peptide comprises a contiguous stretch of amino acids having the consensus amino acid sequence:

```
                                        (SEQ ID NO: 14)
Leu-Pro-Val-Ser-Met-Ile-Ile-Ile-Met-Leu.
```

In certain embodiments, $X^1$ is Ile (I), $X^2$ is Ser (S), $X^3$ is Gly (G), $X^4$ is Leu (L), $X^5$ is Ser (S), and $X^6$ is Ala (A). In such embodiments, the peptide comprises a contiguous stretch of amino acids having the consensus amino acid sequence:

```
                                        (SEQ ID NO: 15)
Leu-Pro-Ile-Ser-Met-Gly-Leu-Ile-Ser-Ala.
```

Examples of suitable embodiments include where: $X^1$ is Val and $X^2$ is Ser, $X^1$ is Val and $X^2$ is Asp, $X^1$ is Val and $X^3$ is Val, $X^1$ is Val and $X^3$ is Gly, $X^1$ is Val and $X^3$ is Ile, $X^1$ is Val and $X^4$ is Leu, $X^1$ is Val and $X^4$ is Ile, $X^1$ is Val and $X^5$ is Ser, $X^1$ is Val and $X^5$ is Met, $X^1$ is Val and $X^6$ is Leu, $X^1$ is Val and $X^6$ is Val, $X^1$ is Val and $X^6$ is Ala, $X^1$ is Ile and $X^2$ is Ser, $X^1$ is Ile and $X^2$ is Asp, $X^1$ is Ile and $X^3$ is Val, $X^1$ is Ile and $X^3$ is Gly, $X^1$ is Ile and $X^3$ is Ile, $X^1$ is Ile and $X^4$ is Leu, $X^1$ is Ile and $X^4$ is Ile, $X^1$ is Ile and $X^5$ is Ser, $X^1$ is Ile and $X^5$ is Met, $X^1$ is Ile and $X^6$ is Leu, $X^1$ is Ile and $X^6$ is Val, $X^1$ is Ile and $X^6$ is Ala, $X^2$ is Ser and $X^3$ is Val, $X^2$ is Ser and $X^3$ is Gly, $X^2$ is Ser and $X^3$ is Ile, $X^2$ is Ser and $X^4$ is Leu, $X^2$ is Ser and $X^4$ is Ile, $X^2$ is Ser and $X^5$ is Ser, $X^2$ is Ser and $X^5$ is Met, $X^2$ is Ser and $X^6$ is Leu, $X^2$ is Ser and $X^6$ is Val, $X^2$ is Ser and $X^6$ is Ala, $X^2$ is Asp and $X^3$ is Val, $X^2$ is Asp and $X^3$ is Gly, $X^2$ is Asp and $X^3$ is Ile, $X^2$ is Asp and $X^4$ is Leu, $X^2$ is Asp and $X^4$ is Ile, $X^2$ is Asp and $X^5$ is Ser, $X^2$ is Asp and $X^5$ is Met, $X^2$ is Asp and $X^6$ is Leu, $X^2$ is Asp and $X^6$ is Val, $X^2$ is Asp and $X^6$ is Ala, $X^3$ is Val and $X^4$ is Leu, $X^3$ is Val and $X^4$ is Ile, $X^3$ is Val and $X^5$ is Ser, $X^3$ is Val and $X^5$ is Met, $X^3$ is Val and $X^6$ is Leu, $X^3$ is Val and $X^6$ is Val, $X^3$ is Val and $X^6$ is Ala, $X^3$ is Gly and $X^4$ is Leu, $X^3$ is Gly and $X^4$ is Ile, $X^3$ is Gly and $X^5$ is Ser, $X^3$ is Gly and $X^5$ is Met, $X^3$ is Gly and $X^6$ is Leu, $X^3$ is Gly and $X^6$ is Val, $X^3$ is Gly and $X^6$ is Ala, $X^3$ is Ile and $X^4$ is Leu, $X^3$ is Ile and $X^4$ is Ile, $X^3$ is Ile and $X^5$ is Ser, $X^3$ is Ile and $X^5$ is Met, $X^3$ is Ile and $X^6$ is Leu, $X^3$ is Ile and $X^6$ is Val, $X^3$ is Ile and $X^6$ is Ala, $X^4$ is Leu and $X^5$ is Ser, $X^4$ is Leu and $X^5$ is Met, $X^4$ is Leu and $X^6$ is Leu, $X^4$ is Leu and $X^6$ is Val, $X^4$ is Leu and $X^6$ is Ala, $X^4$ is Ile and $X^5$ is Ser, $X^4$ is Ile and $X^5$ is Met, $X^4$ is Ile and $X^6$ is Leu, $X^4$ is Ile and $X^6$ is Val, $X^4$ is Ile and $X^6$ is Ala, $X^5$ is Ser and $X^6$ is Leu, $X^5$ is Ser and $X^6$ is Val, $X^5$ is Ser and $X^6$ is Ala, $X^5$ is Met and $X^6$ is Leu, $X^5$ is Met and $X^6$ is Val, and $X^5$ is Met and $X^6$ is Ala.

In certain embodiments, the peptide may comprise a contiguous stretch of amino acids having the consensus amino acid sequence:

Leu-Pro-Val-X-Met-Val-Leu-Ile-Ser-Leu  (Formula II)

wherein X is any amino acid (SEQ ID NO:17).

In some such embodiments, X is Ser (S) or Asp (D). As such, in some embodiments, X is Ser (S) and the peptide comprises a contiguous stretch of amino acids having the consensus amino acid sequence: LPVSMVLISL (SEQ ID NO:12). In some embodiments, X is Asp (D) and the peptide comprises a contiguous stretch of amino acids having the consensus amino acid sequence: LPVDMVLISL (SEQ ID NO:11).

In certain cases, the kits may include a peptide(s) having at least 60% sequence identity to the amino acid sequence of a human Aquaphorin-4 (AQP-4) peptide having the amino acid sequence: LPVDMVLISL (SEQ ID NO:11), wherein the peptide is up to 50 amino acids in length. The kit may contain the peptide(s) in a solid, semi-solid, liquid, or fluid state. The kit may include one or multiple containers containing specified quantities of the peptide(s). In certain embodiments, the kit may include multiple containers containing the subject peptides described herein unit dosage form.

In certain embodiments, the kit may further include reagents and instructions for carrying out diagnosing, treating, or screening methods using the peptides.

EXAMPLES

The following example is provided to further illustrate the advantages and features of the present invention, but is not intended to limit the scope of the invention. While they are typical of those that might be used, other procedures, methodologies, or techniques known to those skilled in the art may alternatively be used.

Materials and Methods

Patients.

Fifteen NMO patients (12 females and 3 males, 44.3+/−13.8 years) fulfilling Mayo Clinic diagnostic criteria (Wingerchuk D M, et al., Neurology. 2006 May 23; 66(10):1485-9) and nine HC (5 females and 4 males, 40.8+/−10.7 years) were recruited from the UCSF MS Center. A majority of NMO patients had been treated with rituximab (Jacob A, et al., Arch Neurol. 2008 November; 65(11):1443-8), and none had been treated with azathioprine, mycophenolate mofetil, cyclophosphamide or other immunosuppressive medications. None of the patients had received steroids within two months preceding blood draws. Blood was collected by venipuncture. This study was approved by UCSF Committee on Human Research (Protocol #10-00650) and written informed consent was obtained from subjects prior to enrollment.

T Cell Proliferation Assays.

Peripheral blood mononuclear cells (PBMC) were isolated by density gradient centrifugation over Ficoll (Ficoll-Paque PLUS, GE Healthcare) according to manufacturer's instruction. T cell proliferation was evaluated by [$^3$H] thymidine incorporation or CFSE dilution assays. In thymidine incorporation assays, PBMC were cultured with antigens in 96-well plates at either $1 \times 10^5$ cells (AQP4 pools—in at least 10 wells) or $5 \times 10^5$ cells (individual peptides—in duplicate) per well for 6 days (d). Cultures were then pulsed with [$^3$H] thymidine and harvested 18 h later. Positive wells were defined as having counts-per-minute (cpm) values greater than control cpm average values+3 standard deviation (SD) or stimulation index (SI) greater than 2. Alternatively, PBMC were stained with 1 μM CFSE (Invitrogen), according to manufacturer's instruction. Cells were cultured in the presence of antigens for 10 d. T cell proliferation was assessed by flow cytometric evaluation of CFSE dilution. Proliferation was expressed as the cell division index (CDI) (defined as the number of CFSE$^{low}$ T cells cultured with antigen/number of CFSE$^{low}$ T cells without antigen). In all cases, culture medium consisted of X-VIVO 15 (Lonza) supplemented with penicillin (100 U/ml) and streptomycin (0.1 mg/ml).

Antigens.

Peptides were synthesized by Genemed Synthesis Inc. with purity greater than 95% by HPLC analysis. Overlapping AQP4 20-mer peptides were offset by 10 amino acids. Peptides corresponding to certain hydrophobic AQP4 sequences were synthesized in overlapping 15-mer peptide pairs. Truncated peptides within the 61-80 region (p61-78 GTEKPLPVDMVLISLCFG (SEQ ID NO:18); p61-76 GTEKPLPVDMVLISLC (SEQ ID NO:19); p61-74 GTEKPLPVDMVLIS (SEQ ID NO:20); p61-72 GTEKPLPVDMVL (SEQ ID NO:21); p63-80 EKPLPVDMVLISLCFGLS (SEQ ID NO:22); p65-80 PLPVDMVLISLCFGLS (SEQ ID NO:23); p67-80 PVDMVLISLCFGLS (SEQ ID NO:24); p69-80 DMVLISLCFGLS (SEQ ID NO:25), AQP4 p63-76 (EKPLPVDMVLISLC, SEQ ID NO:7) and bacterial peptide ABC/TP p204-217 (FIILPVSMVLISLV, SEQ ID NO:8) were as quoted. Full length recombinant human (rh) AQP4 (1-323) was expressed in *Pichia pastoris* and purified as described (Ho J D, et al., Proc Natl Acad Sci USA. 2009 May 5; 106(18):7437-42). Tetanus toxoid was obtained from List Biological Laboratories, Inc. (Campbell, Calif.).

Flow Cytometry Analysis.

Single-cell suspensions were incubated with human serum to prevent nonspecific antibody binding, then stained with anti-CD3, -CD4, -CD8, -CD25, -MHC Class II, -CD40, -CD80, and -CD86 (eBioscience and BD Bioscience). Intracellular cytokine production by CD4$^+$ T cells and APC was analyzed by monitoring the expression of IFN-γ, IL-17, IL-6, IL-1β and IL-10 (1:100) (eBioscience). Foxp3 staining was performed according to the manufacturer's protocol (eBioscience). For intracellular cytokine staining, T cells were stimulated with phorbol 12-myristate 13-acetate (PMA, 50 ng/ml) plus ionomycin (500 ng/ml) in the presence of GolgiStop (1 μl/ml) (BD Biosciences). CD14$^+$ cells were stimulated with LPS (1 μg/ml; Sigma-Aldrich) for 4 or 20 h in the presence of GolgiStop. Cells were analyzed by flow cytometry on a FACS Canto flow cytometer (BD Biosciences).

Blocking of HLA Alleles with Antibodies.

Inhibition of the proliferation of PBMC to AQP4 p61-80 and rhAQP4 was studied by using mouse monoclonal anti-HLA-DR (clone G46-6; BD Bioscience, Mississauga, ON, Canada), anti-HLA-DQ (clone HG-38; Abcam), anti-HLA-DP (clone B7/21; Abcam) and isotype control (clone G155-178; BD Biosciences). Antibodies (1 μg/ml) were added to CFSE-stained PBMC cultures 1 hour before addition of antigens.

Antigen Recall Experiments.

PBMC were initially stimulated with antigens. After 10 d, cells were restimulated with rhAQP4 (5 μg/ml), AQP4 peptides or bacterial peptide (10 μg/ml), in the presence of irradiated autologous APC. Following 3 d of stimulation, cultures were pulsed with [$^3$H]thymidine and harvested 18 h later.

Stimulation Index (SI) was calculated by dividing cpm in wells with antigen by cpm in control wells with no antigen of each assay test group.

Analyses for Protein Sequence Homology and MHC Core Binding Motifs.

Sequences similarities between AQP4 and other proteins were addressed using the protein-protein Basic Local Alignment Search Tool (BLAST) from NCBI. The prediction of the core binding motif within AQP4 61-80 sequence for HLA-DRB1*0301 and HLA-DRB3*0202 was performed with net-MHCII-1.1 (Nielsen M, et al., BMC Bioinformatics. 2007; 8:238) and net MHCII-2.2 (Nielsen M, et al., BMC Bioinformatics. 2009; 10:296), programs that utilizes relative affinities of identified determinants from the immune epitope database (IEDB).

HLA Typing.

High-resolution HLA typing was performed by the UCSF Immunogenetics and Transplantation Laboratory (ITL, UCSF Department of Surgery). The following HLA loci were analyzed using sequence-based typing: DRB1, DRB3/4/5, DQA1, DQB1, DPA1, and DPB1. Sequence ambiguities outside exon 2 were resolved.

Statistics.

Figure 3A:
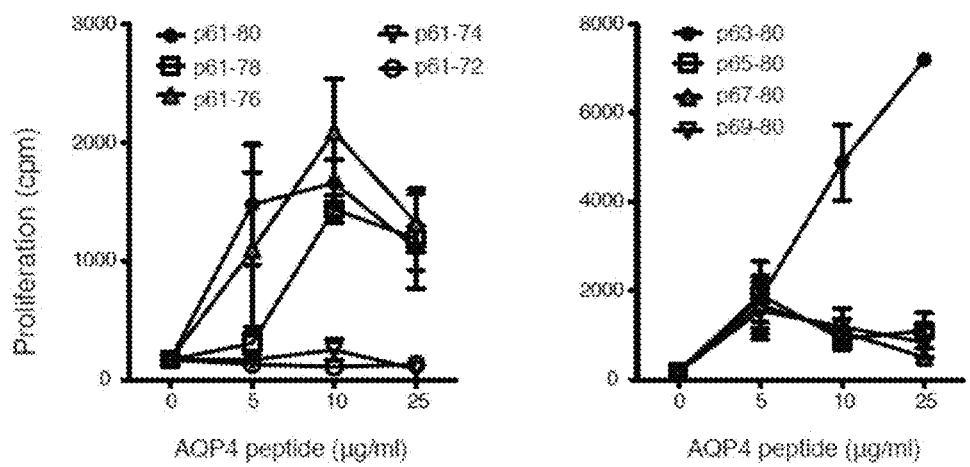
Figure 3B:
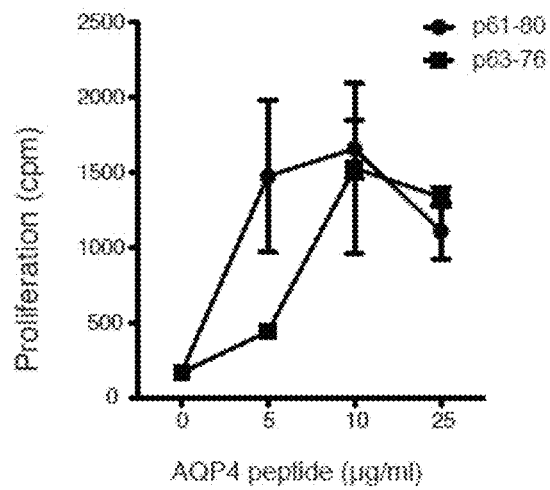
Figure 3E:
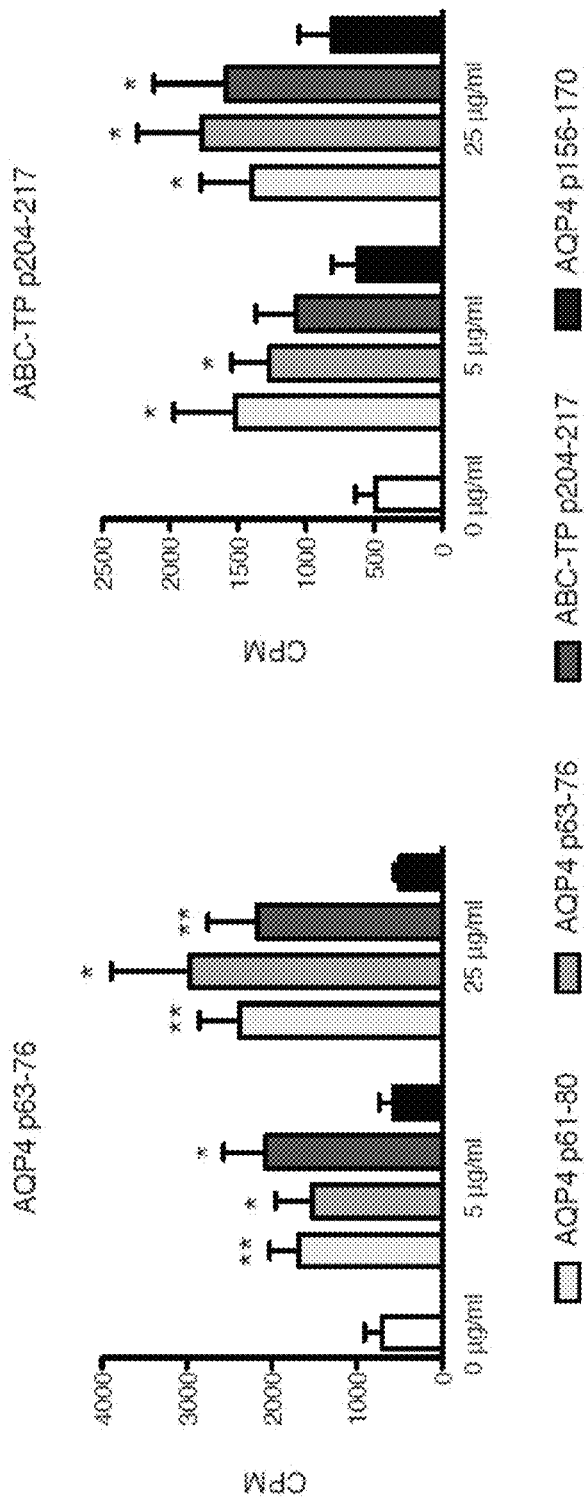

Statistical analysis was performed using either GraphPad Prism software or STATA. The nonparametric Mann-Whitney U test was used to compare data. Paired t-tests were performed to compare cpm values with antigens to control values with no antigens presented in FIG. 3E. A value of P≤0.05 was considered significant.

Example 1

T Cells from NMO Patients Recognize Discrete AQP4 Determinants and are Restricted by HLA-DR Molecules In general, antigen-specific T cells recognize linear peptide fragments of 10-15 amino acids in association with MHC (HLA) proteins expressed on APC (Zamvil S S, et al., Nature. 1986 Nov. 20-26; 324(6094):258-60). In order to identify AQP4-specific T cells in NMO patients, proliferation of peripheral blood mononuclear cells (PBMC) to a library of 32 synthetic overlapping 15 mer and 20 mer peptides encompassing the 323 amino acid sequence of full-length human AQP4 (M1 isoform) was initially tested. Here, separate pools containing five overlapping AQP4 peptides were studied. By [$^3$H] thymidine incorporation, more frequent proliferative responses in primary cultures to AQP4 pools 1-55, 46-100, 126-170, 201-250 and 241-300 was detected (FIG. 1A). Lymphocytes from healthy controls (HC) also proliferated to some of these pools, and exhibited comparable responses to tetanus toxoid (TT).

Figure 1B:
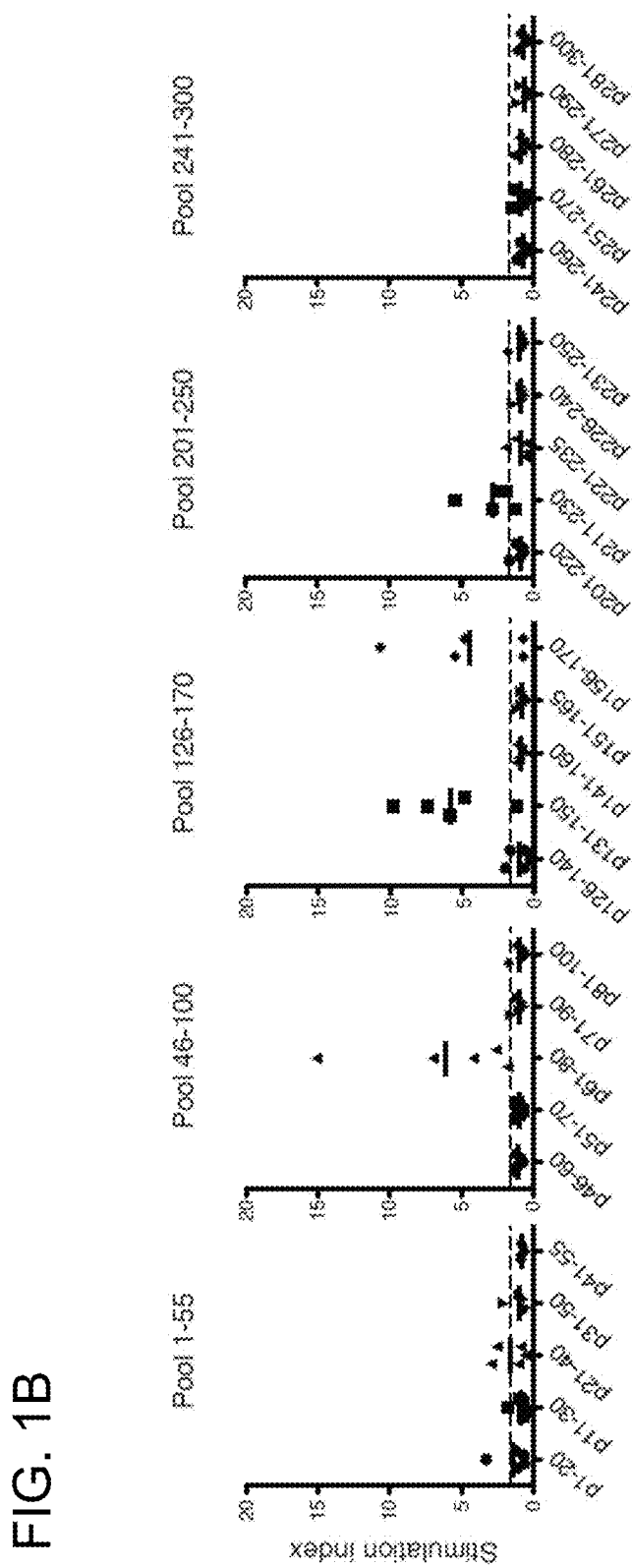
Figure 1C:
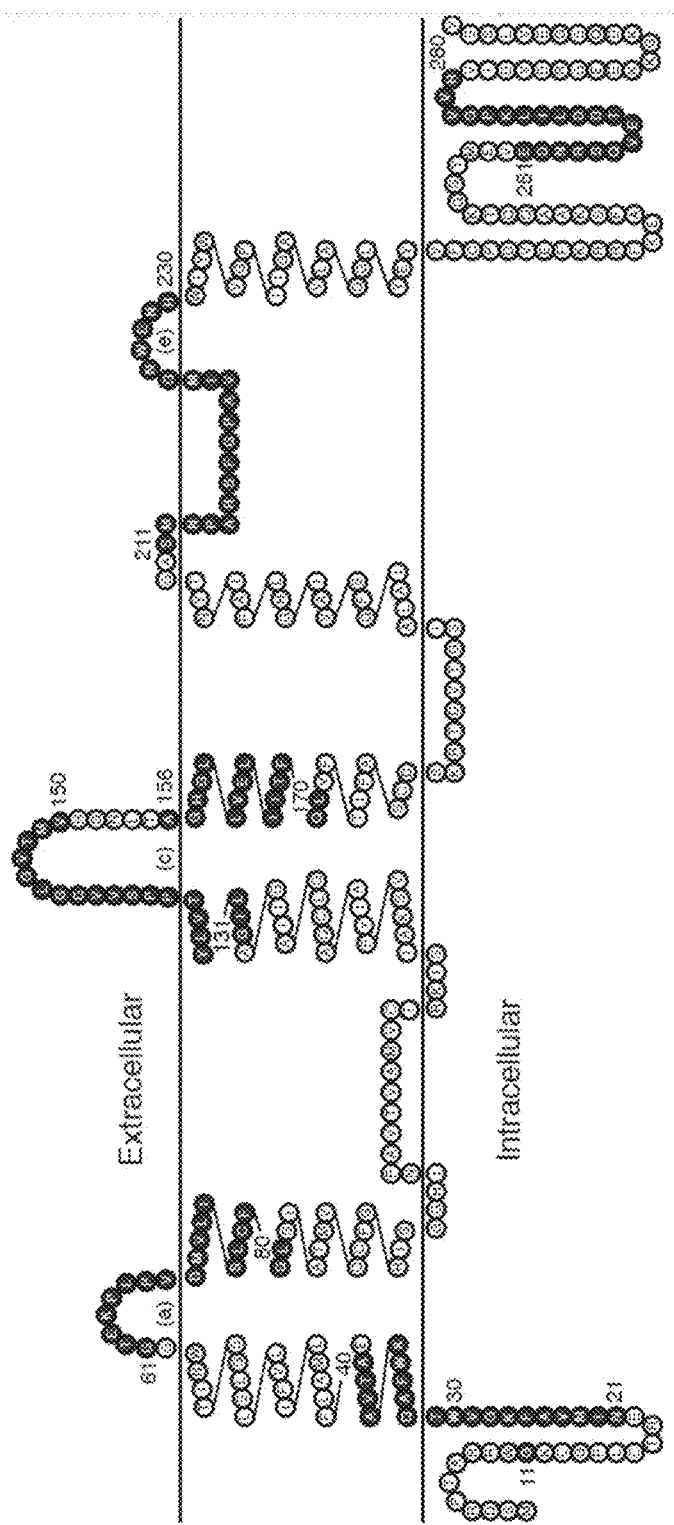
FIG. 1C shows topological diagram of human AQP4 (SEQ ID NO:9).
Figure 1E:
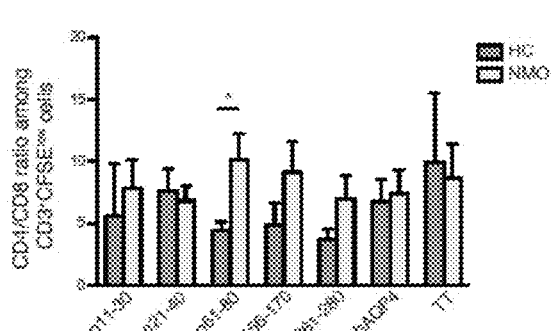

Having identified candidate regions of AQP4 containing T cell determinants, proliferative responses of NMO patients to individual AQP4 peptides was then tested. T cell determinants were identified within peptides (p) 21-40, 61-80, 131-150, 156-170 and 211-230 (FIG. 1B), which corresponded to intracellular, extracellular and transmembrane sequences of AQP4 (FIG. 1C). Interestingly, three of these AQP4 determinants, p61-80, p131-150 and p211-230, respectively, are located in extracellular A, C and E loops, AQP4 domains targeted by NMO-IgG (Owens G, et al., Mult Scler. 2011; 17(10 Suppl):S291-S2). The fluorescent dye 5,6-caroxylfluorescein diacetate succinimidyl ester (CFSE) dilution assay is considered a more powerful and sensitive method for detecting proliferation of rare autoantigen-specific human T cells than the traditional [$^3$H]thymidine incorporation (Mannering S I, et al., J Immunol Methods. 2003 December; 283(1-2): 173-83). Using this approach, responses to individual AQP4 peptides identified in the initial screening, and also to AQP4 T cell determinants common to mouse strains with distinct MHC haplotypes was examined (Nelson P A, et al., PLoS One. 2010 November 2010; 5(11):e15050 1-9; Kalluri S R, et al., PLoS ONE. 2011; 6(1):e16083). A robust proliferative T cell response to p61-80, which is located within the extracellular A loop, was detected in all NMO patients tested. T cell responses were observed to AQP4 p21-40, p156-170, p11-30 and p261-280 (FIG. 1D), even though substantial proliferation to the latter two peptides in the initial [$^3$H]thymidine incorporation assays was not detected. T cells from HC also recognized these AQP4 peptides, but again, the proliferative responses were both lower and less frequent than in NMO patients. Proliferating AQP4-specific T cells were predominantly CD4$^+$, and the proportion of CD4$^+$ T cells that responded to AQP4 p61-80 was higher in NMO patients than HC (FIG. 1E).

Figure 1F:
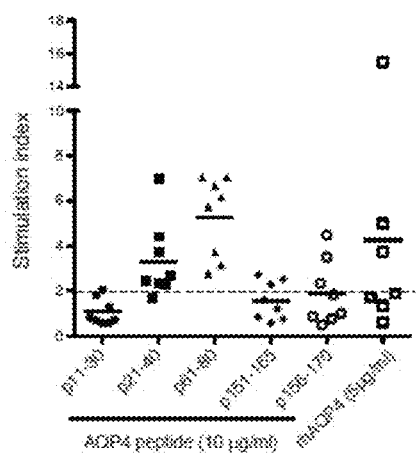

Presentation of native protein antigens by APC generally requires proteolytic processing (Slavin A J, et al., J Clin Invest. 2001; 108(8):1133-9; Soos J M, et al., J Immunol. 1998 Dec. 1; 161(11):5959-66; Zamvil S, et al., Nature. 1985 Sep. 26-Oct. 2; 317(6035):355-8; Vyas J M, et al., Nat Rev Immunol. 2008 August; 8(8):607-18). Therefore, it was examined whether the identified AQP4 peptides contained natural T cell determinants of intact AQP4. When T cells initially stimulated with rhAQP4 were tested for recall responses to individual AQP4 peptides, proliferation to AQP4 p21-40 and p61-80 was observed, indicating that these are naturally processed determinants of AQP4 (FIG. 1F). Among peptides that were examined, AQP4 p61-80 was clearly immunodominant. Several studies have identified over-representation of HLA-DPB1*0501, HLA-DRB1*0301 or HLA-DRB3 in NMO patients (Matsushita T, et al., Tissue Antigens. 2009 February; 73(2):171-6; Brum D G, et al., Mult Scler. 2010 January; 16(1):21-9; Deschamps R, et al., Mult Scler. 2011 January; 17(1):24-31), suggesting these MHC II alleles could serve as restriction elements for CD4$^+$ T cells in NMO. A high representation of these HLA alleles in the patient cohort was also identified, in particular, an over-representation of HLA-DRB3*0202 among NMO subjects was noted (Table 2).

TABLE 2

| | HLA haplotypes of NMO patients and healthy controls | | | | |
|---|---|---|---|---|---|
| | DRB1*1501[a] | DQB1*0602[a] | DRB1*0301[b] | DRB3*0202[b] | DPB1*0501[b] |
| NMO Patients | 3/15 20% | 2/15 13% | 7/15 47% | 11/15 73% | 7/15 47% |
| Healthy Controls | 2/8 25% | 1/8 12.5% | 3/8 37.5% | 3/8 37.5% | 3/8 37.5% |

Figure 2A:
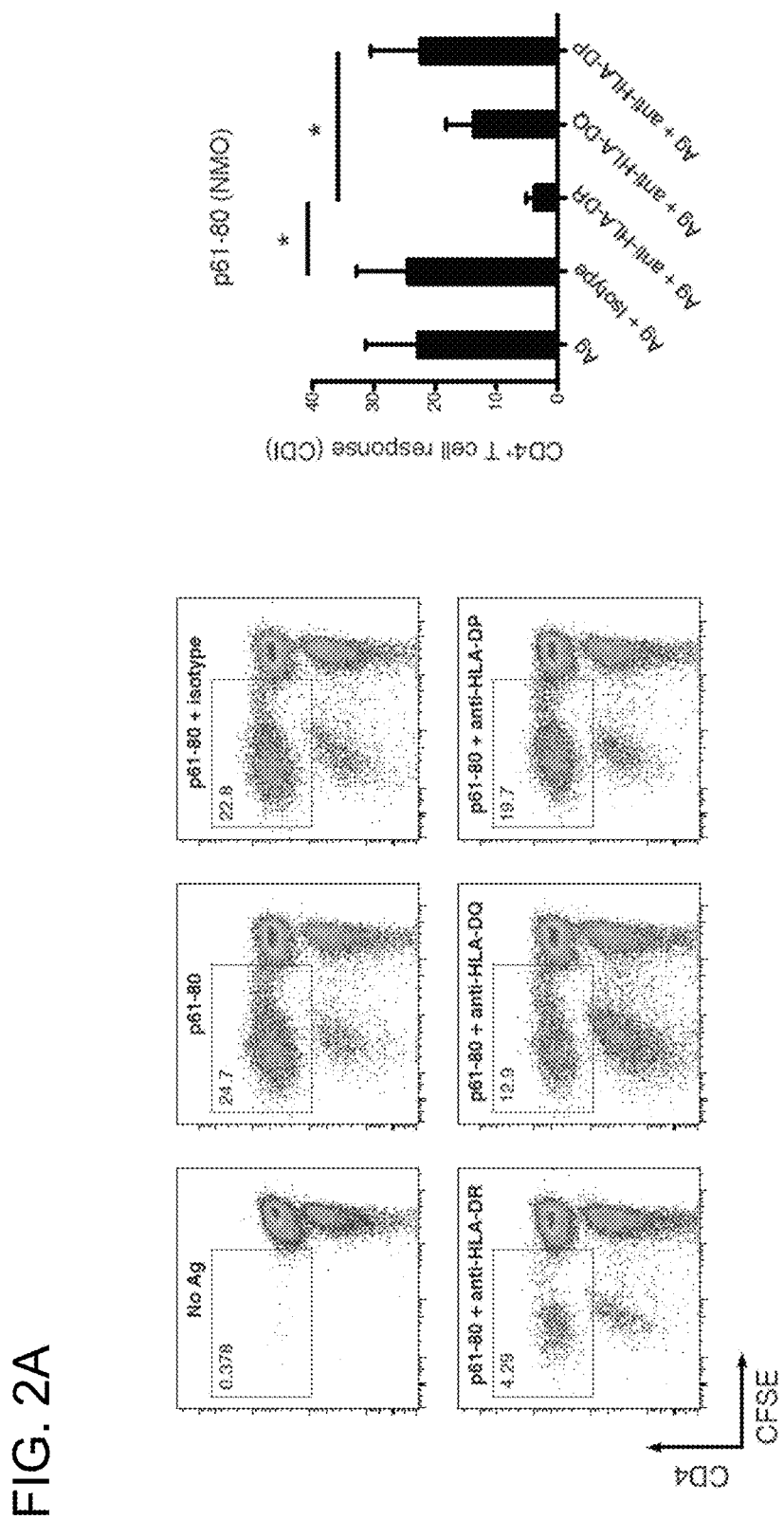
FIG. 2A-2C shows that HLA-DR serves as a restriction element for AQP4-specific T cells.
Figure 2B:
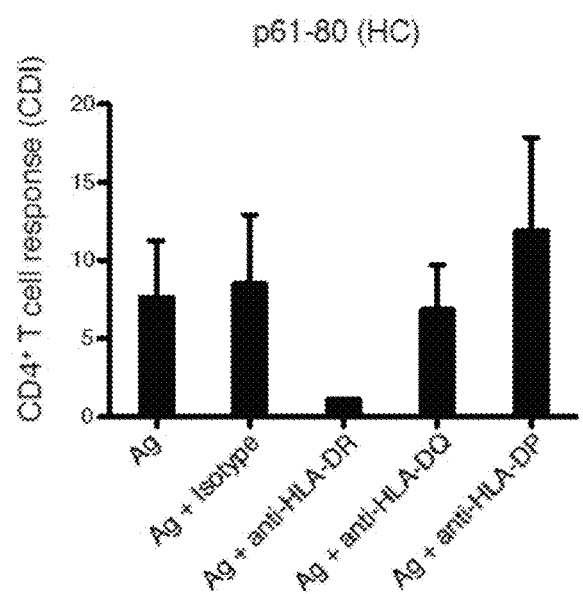

[a]Alleles associated with multiple sclerosis susceptibility;
[b]Alleles associated with neuromyelitis optica susceptibility Using MHC II blocking antibodies, it was observed that T cell proliferative responses to AQP4 p61-80 were inhibited by anti-HLA-DR, but were not statistically inhibited by anti-HLA-DQ or anti-HLA-DP, demonstrating that HLA-DR molecules serve as restriction elements for T cells that recognize this determinant (FIG. 2A). Proliferation of AQP4 p61-80-specific T cells from HLA-matched HC (Table 2) was also inhibited by anti-HLA-DR antibodies (FIG. 2B). Further, a similar MHC II-restriction profile was observed after stimulating T cells from NMO patients with rhAQP4 (FIG. 2C) suggesting that other AQP4 determinants may also be restricted by HLA-DR molecules.

FIGS. 1A-1F. T cells from NMO patients recognize discrete determinants of AQP4. PBMC were tested for proliferation to (Panel A) pools of AQP4 peptides (n=8 NMO and n=3 HC) and to (Panel B) individual AQP4 peptides identified from those pools. In (Panel A and Panel B) PBMC were cultured for 6 d in the presence of AQP4 pools (10 µg/ml) or AQP4 peptides (10 µg/ml), respectively, then pulsed with [$^3$H]thymidine and harvested 18 h later. In (Panel A), positive wells were defined as values>control cpm average values+ 3SD. (Panel C) AQP4 determinants are represented within a human AQP4 topological diagram using Johns S. J., TOPO2, Transmembrane protein display software (Crane J M, et al., Neuroscience. 2010 Jul. 28; 168(4):892-902). (Panel D and Panel E) PBMC were examined by CFSE dilution for proliferation to individual AQP4 peptides (10 µg/ml), rhAQP4 (5 µg/ml) or in (Panel E) tetanus toxoid (TT) (1 µg/ml) after 10 d of culture. CFSE was measured in CD3$^+$, CD4$^+$ and CD8$^+$ T cells by FACS and quantified by cell division index (CDI). CDI>2 (broken lines) was considered positive. (Panel F) Recall T cell proliferation ([$^3$H]thymidine incorporation) to individual AQP4 peptides (10 µg/ml) or rhAQP4 (5 µg/ml) was detected after initial stimulation with rhAQP4 (5 µg/ml) for 10 d. In Panels A and E, error bars indicate SEM; in B, D and F, horizontal lines indicate mean values. *P<0.05 Mann-Whitney U test.

Figure 2C:
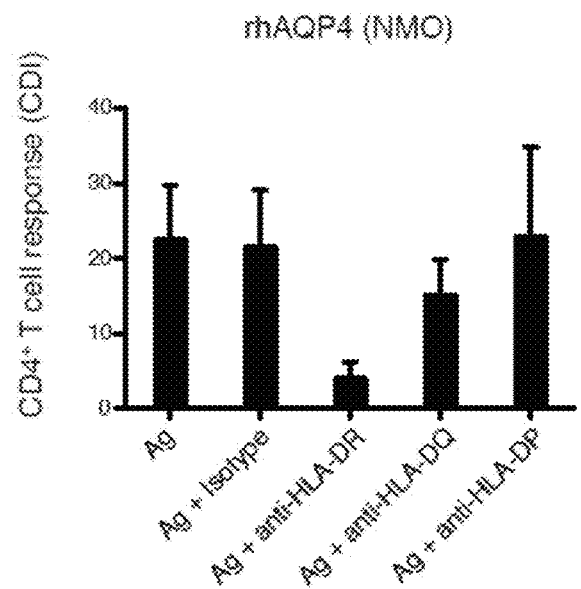

FIG. 2A-2C. HLA-DR serves as a restriction element for AQP4-specific T cells. (Panels A and B) CFSE-labeled PBMC from NMO patients were cultured for 10 d with antigens alone or in combination with anti-HLA-DR, -HLA-DQ, -HLA-DP or isotype control antibodies. T cell proliferation was evaluated by FACS analysis of CFSE dilution. Inhibitory effects of blocking antibodies were examined on proliferating CD4$^+$ T cells (n=7 NMO in (Panel A) and n=4 NMO in (Panel B)). T cell proliferation is expressed as cell division index (CDI). (Panel C) PBMC from HC were similarly examined after stimulation with AQP4 p61-80 (n=2). Error bars represent SEM. *P<0.05, Mann-Whitney U test.

Example 2

AQP4 P63-76-Specific T Cells Cross-React with *C. Perfringens* ABC Transporter Permease P204-217

In order to characterize the fine specificity of AQP4 p61-80-specific T cells, proliferation to truncated peptides corresponding to sequences within this region was examined. AQP4 p61-80-specific T cells proliferated in response to p61-78 and p61-76 but not to p61-74 or p61-72 (FIG. 3A). Shorter AQP4 peptides truncated from the N-terminal sequence, p65-80, p67-80 and p69-80 also stimulated proliferation of p61-80-specific T cells although less efficiently than p63-80. Collectively, these findings indicated that p63-76 contained the core determinant of AQP4 61-80. In this regard, it was observed that p61-80-specific T cells responded nearly as efficiently to p63-76 as to p61-80 (FIG. 3B). Interesting, AQP4 63-76 contains the predicted binding motif for HLA-DRB1*0301 and HLA-DRB3*0202 (FIG. 3C).

Immune responses to pathogens may elicit cross-reactivity to self-antigens that share structural or sequence homology (Fujinami R S, Oldstone M B. Science. 1985 Nov. 29; 230 (4729):1043-5; Wucherpfennig K W, Strominger J L. Cell. 1995 Mar. 10; 80(5):695-705). This process, known as 'molecular mimicry', is considered one important potential mechanism in autoimmunity. Having found that p63-76 contains an immunodominant AQP4 T cell epitope, whether this sequence might share homology with other proteins was addressed. 90% homology between AQP4 66-75 and the ten amino acid sequence 207-216 within conserved ABC transporter permease (ABC-TP) proteins from several strains of the bacterium *Clostridium perfringens* (NCBI protein reference sequences ZP_02952885.1, ZP_02638213.1, ZP_02634520.1, ZP_02630305.1; 90% positives, 90% identities, 0% gaps) was identified (FIG. 3C). T cells from NMO patients proliferated significantly to ABC-TP p204-217, although less intensely than to AQP4 p61-80 and AQP4 p63-76 (FIG. 3D). To directly test for cross-reactivity, T cells initially stimulated with AQP4 p63-76 or ABC-TP were tested for recall responses in a reciprocal manner (FIG. 3E). Importantly, AQP4-primed T cells proliferated to ABC-TP p204-217 and vice versa, supporting molecular mimicry between this bacterial transmembrane protein and AQP4. Confirming specificity of those recall responses, proliferation to p156-170 was not observed.

FIG. 3A-3E. Cross-reactivity between AQP4 p63-76 and *Clostridium perfringens* ABC transporter permease (ABC/TP) p204-217. (Panel A) The T cell epitope within AQP4 p61-80 was mapped by testing recall proliferation of AQP4 p61-80-reactive T cells from NMO patients to truncated AQP4 peptides (10 μg/ml) in the presence of irradiated autologous APC. (Panel B) AQP4 p63-76 appeared to contain p61-80 core determinant. Proliferation was measured by [$^3$H] thymidine incorporation after 3 d. Data are representative of three independent experiments. (Panel C) Sequence homology between AQP4 p63-76 and *C. perfringens* ABC transporter permease (ABC-TP) p204-217 was identified using the protein-protein Basic Local Alignment Search Tool (BLAST) from NCBI. Top bracket represents the predicted core binding motif for HLA-DRB1*0301 and HLA-DRB3*0202 within AQP4 p63-76 (netMHCII-1.1 and -2.2 programs). (Panel D) CFSE-labeled PBMC from 3 NMO patients were stimulated with antigens (10 μg/ml) and cultured for 10 d before evaluating proliferation by FACS. (Panel E) PBMC from 4 NMO patients were initially stimulated for 10 d with AQP4 p63-76 or ABC/TP p204-217 at 10 μg/ml. Recall responses to peptides in the presence of irradiated autologous APC were evaluated by [$^3$H]thymidine incorporation after 3 d. Paired t-tests were performed to compare counts per minute (cpm) values of each antigen to cpm values of no-antigen controls, *P<0.05, **P<0.01. In (Panel A), (Panel B) and (Panel E) data are presented as means of duplicate or triplicate wells; in (Panels A-E) error bars indicate SEM.

Example 3

AQP4 P61-80-Specific T Cells from NMO Patients Exhibit Pro-Inflammatory Th17 Polarization Although indirect, some clinical and histologic data suggest Th17 cells may participate in NMO pathogenesis (Lucchinetti C F, et al. Brain. 2002 July; 125(Pt 7):1450-61; Warabi Y, et al., J Neurol Sci. 2006 Nov. 15; 249(2):145-52). Thus, proinflammatory cytokine production in proliferating

Figure 4A:
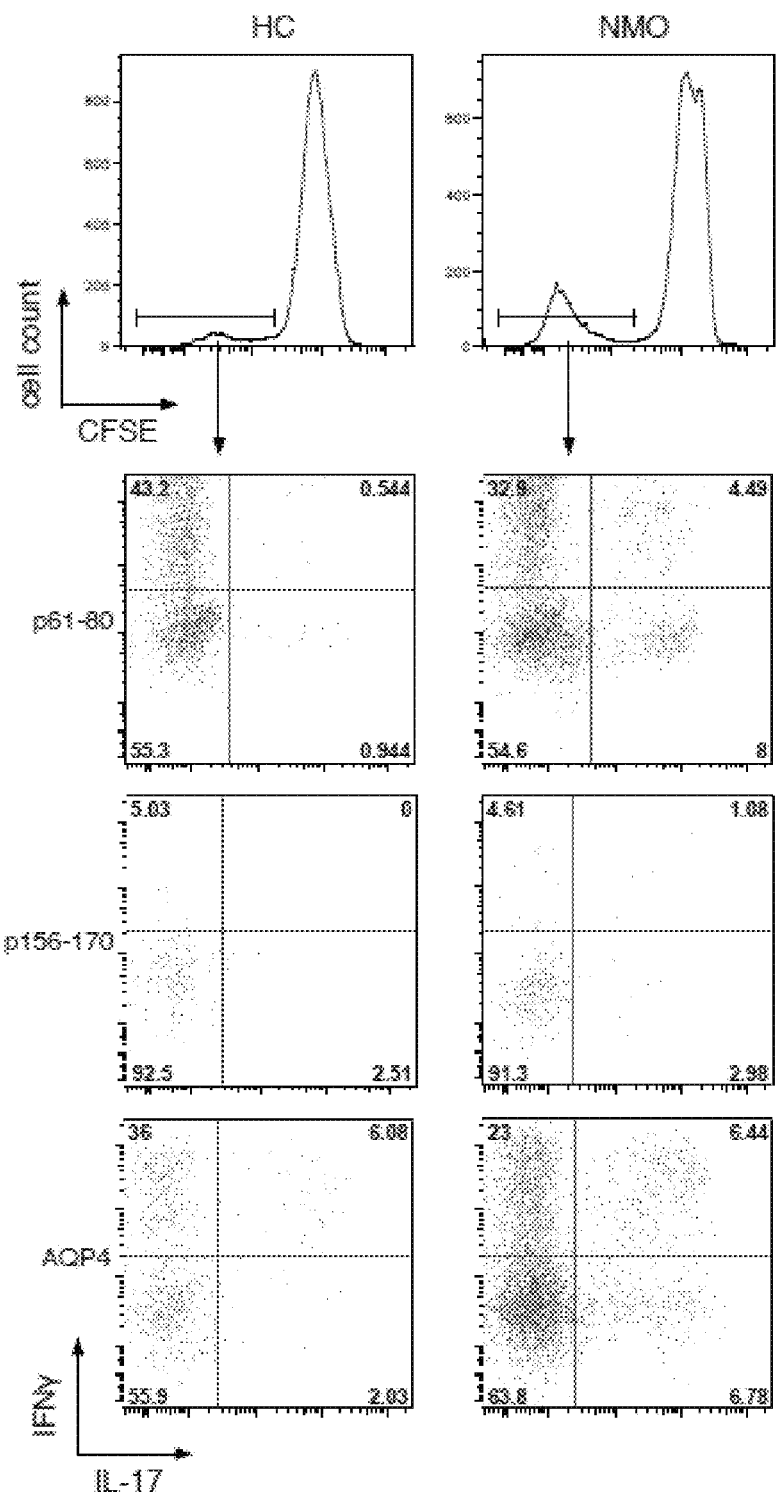
FIG. 4A-4D shows that AQP4 p61-80-specific T cells exhibit a pro-inflammatory bias.
Figure 4B:
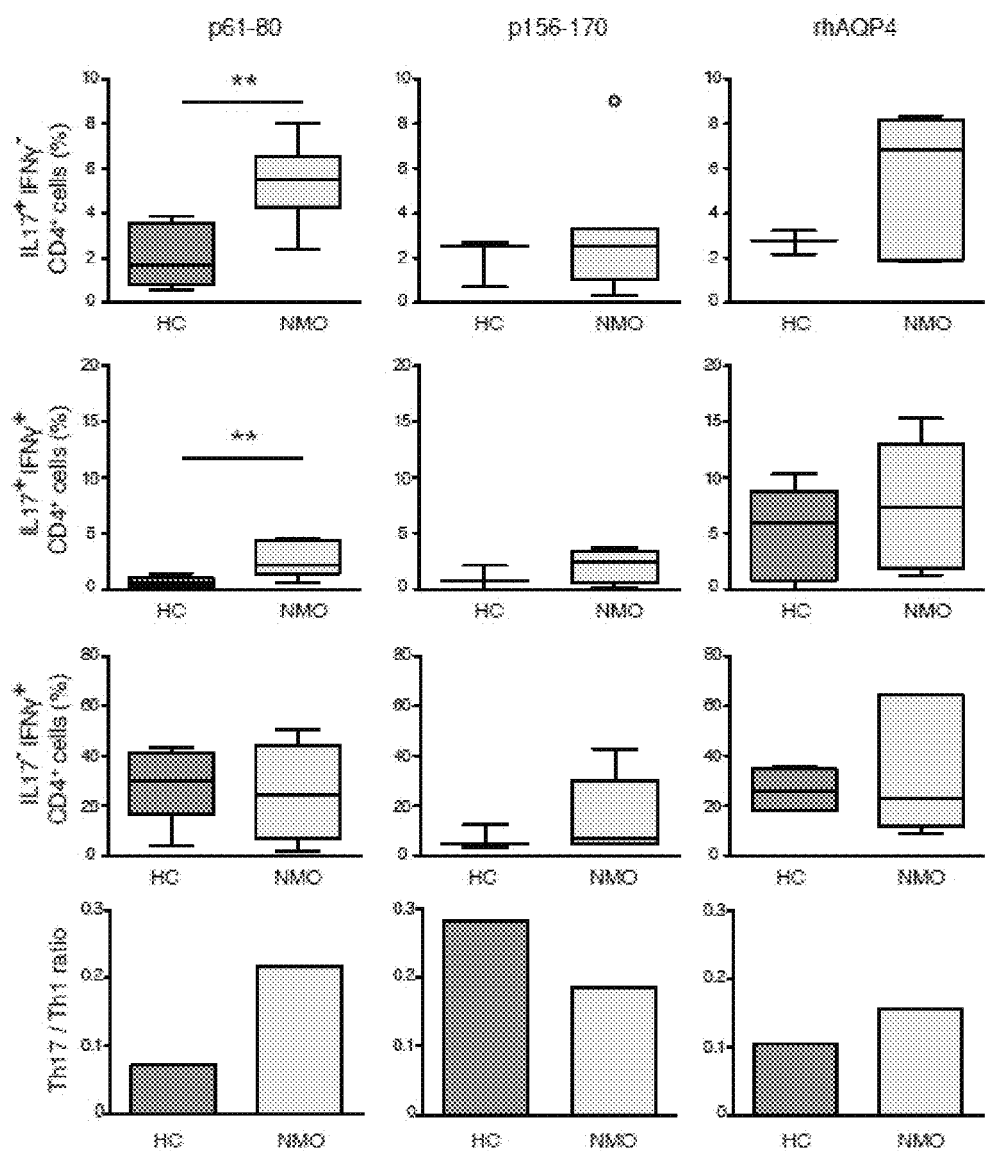
Figure 4C:
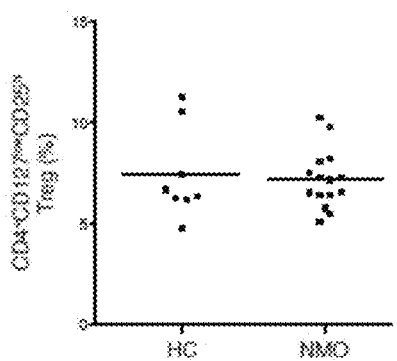
Figure 4D:
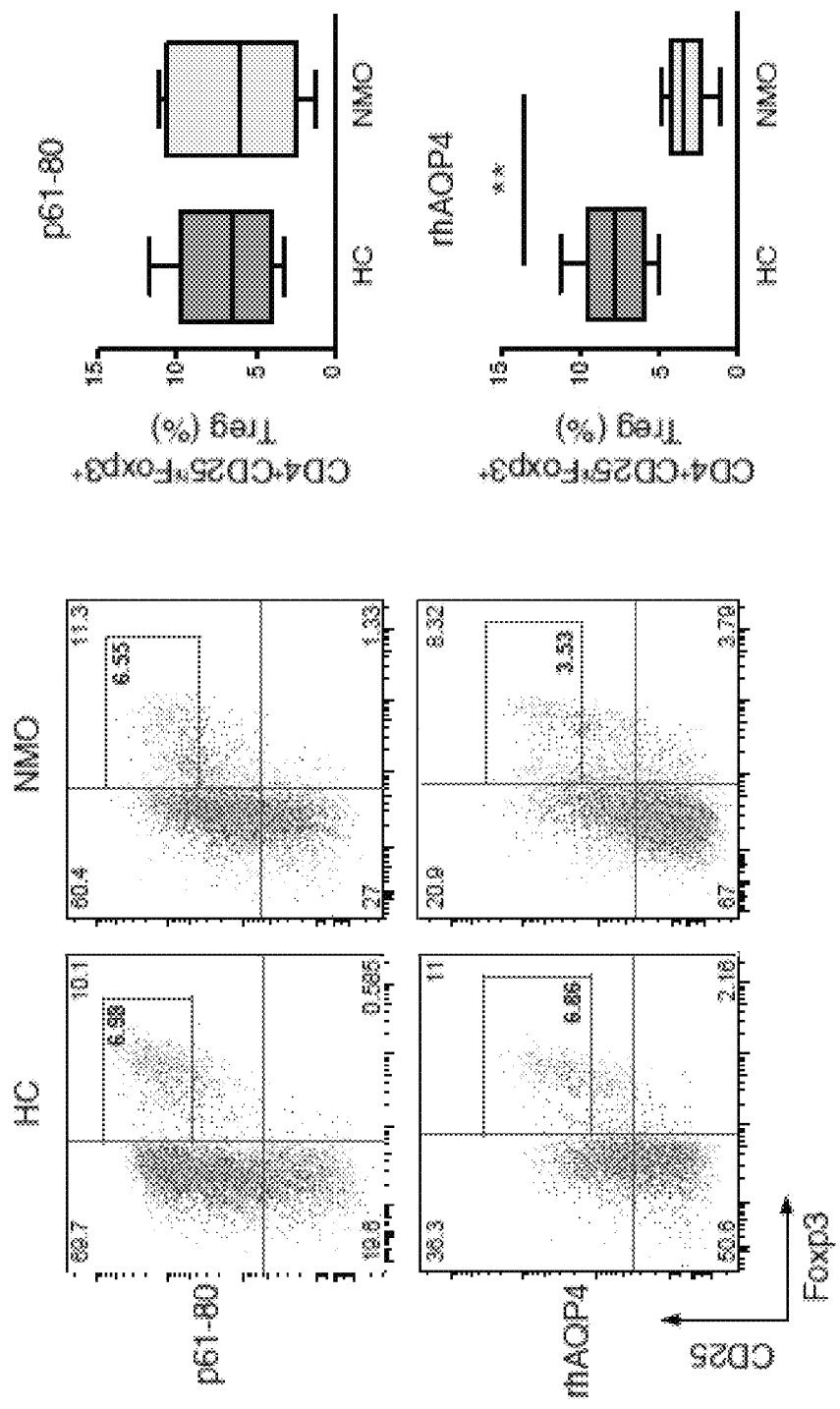

AQP4-specific T cells was examined. In comparison to HC, significantly higher frequencies of IL-17+ single- and IL-17+ IFN-γ+ double-positive cells that recognized p61-80 in NMO patients was observed (FIG. 4A, B). An increased frequency of Th17 cells from NMO patients was observed after stimulation with rhAQP4, but was not significant. No Th17 bias was detected in response to AQP4 p156-170, suggesting the Th17 polarization may be epitope-specific. In contrast, IFN-γ production by AQP4-specific T cells appeared unchanged between the two groups. Thus, the Th17/Th1 ratio was elevated in NMO patients in response to the immunodominant determinant AQP4 p61-80, but not to the other antigens tested. Interestingly, a difference in the frequency of peripheral blood regulatory T cells (Treg) from NMO patients and HC was not detected (FIG. 4C). By contrast, the examination of AQP4-specific T cells revealed a significantly reduced frequency of Treg in NMO patients in response to rhAQP4, but not to p61-80 (FIG. 4D).

FIG. 4A-4D. AQP4 p61-80-specific T cells exhibit a proinflammatory bias. PBMC were stained with CFSE and cultured for 10 d with AQP4 peptides (10 μg/ml) or rhAQP4 (5 μg/ml). (Panel A) CD4+CFSE$^{low}$ proliferating T cells were analyzed for IL-17 and IFN-γ production by intracellular staining after stimulation with PMA/Ionomycin for 5 h. (Panel B) Frequencies of IL17+IFN-γ−, IL17+IFN-γ+ and IL17−IFN-γ+ were examined among proliferating p61-80-specific CD4+ T cells (n=8 NMO and n=5 HC), p156-170-specific CD4+ T cells (n=6 NMO and n=3 HC) and rhAQP4-specific CD4+ T cells (n=6 NMO and n=5 HC). Frequencies of IL-17- and IFN-γ-single positive T cells were used to calculate Th17/Th1 ratio. (Panel C) PBMC were examined by FACS for expression of Treg markers including CD4, CD127 and CD25. (Panel D) CFSE-labeled PBMC were cultured for 10 d with AQP4 p61-80 (10 μg/ml) or rhAQP4 (5 μg/ml). Proliferating CD4+ T cells (CDI>2) were examined by FACS for expression of CD25$^{high}$, defined as the top half of CD25+ cells, and Foxp3 (n=8 NMO p61-80, n=6 HC p61-80, n=7 NMO rhAQP4 and n=5 HC rhAQP4). Box-and-whisker plots include the median, distribution and range. **$P<0.01$ Mann-Whitney U test.

Example 4

Monocytes from NMO Patients Exhibit Pro-Inflammatory Polarization

Antigen presenting cells (APC), including monocytes and other myeloid cells, express costimulatory molecules and secrete specific cytokines that participate in activation and promote lineage commitment of antigen-specific T cells. In this regard, IL-6 is critical for Th17 differentiation (Acosta-Rodriguez E V, et al. Nat Immunol. 2007 September; 8(9): 942-9). Previous studies have indicated that serum IL-6 levels are elevated in NMO patients (Uzawa A, et al. Mult Scler. 2010 December; 16(12):1443-52). Since AQP4 p61-80-specific T cells from NMO patients exhibited Th17 polarization, whether there were alterations in expression of costimulatory molecules or increased production of IL-6 by myeloid APC was addressed. In comparison to HC, there was no evident change in frequency of peripheral blood monocytes. However, increased expression of CD40 and CD80 (FIG. 5A; histogram for healthy control is located in between the histograms for isotype and NMO patient), costimulatory molecules that can be associated with pro-inflammatory T cell polarization was observed (Katzman S D, et al., J Immunol. 2011 Apr. 15; 186(8):4668-73; Kuchroo V K, et al., Cell. 1995 Mar. 10; 80(5):707-18). The frequency of IL-6-producing monocytes was similar in NMO patients and HC. Nevertheless, there were both relative and absolute increases of intracellular IL-6 production after LPS stimulation in monocytes from NMO patients (FIG. 5B, C). No such differences were observed in expression of IL-1β and IL-10. These results indicate that in addition to the known involvement of adaptive immunity, phenotypic changes of cells within the innate immune system may also contribute to NMO pathogenesis.

Figure 5A:
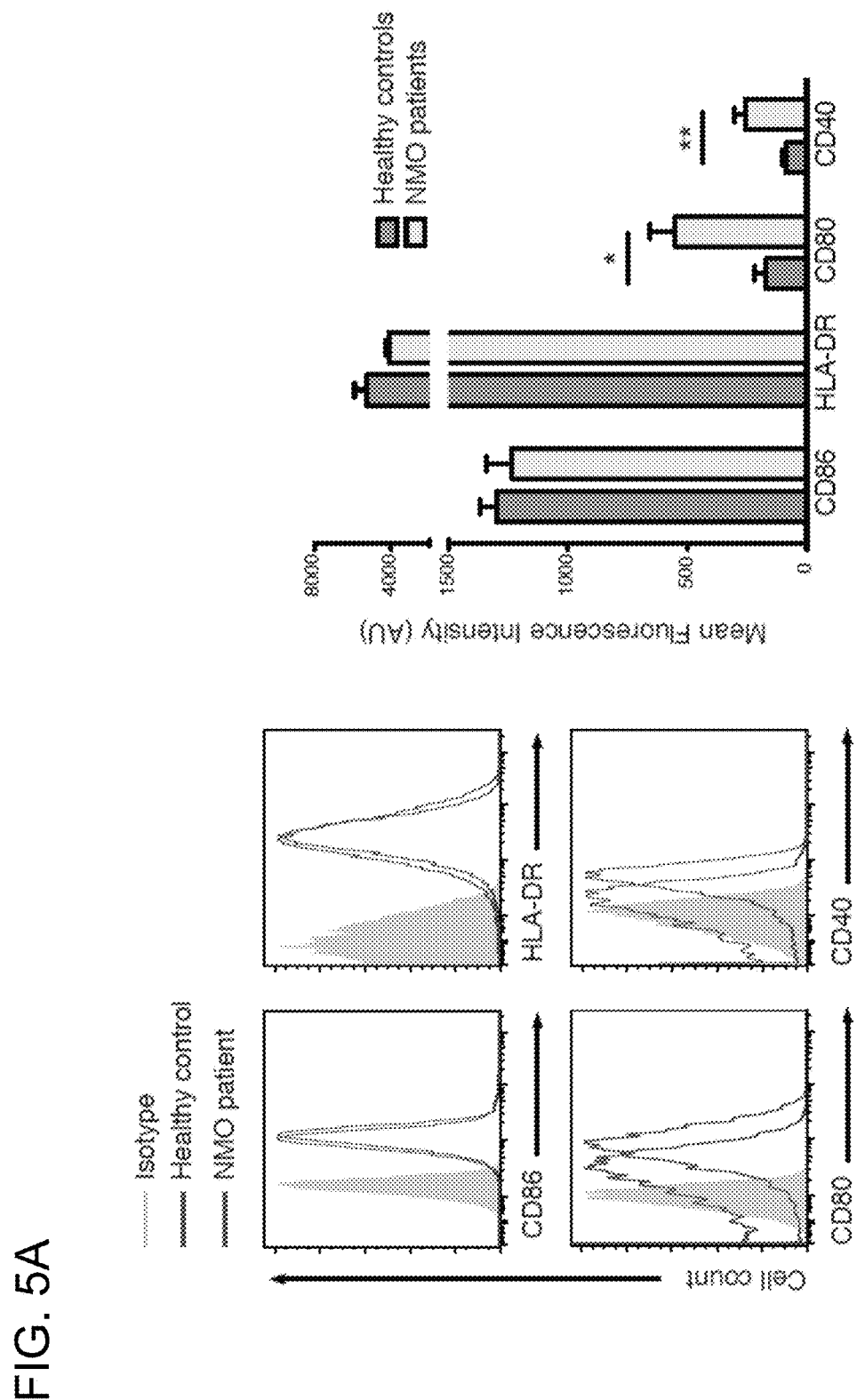
FIG. 5A-5C shows CD14+ monocytes from NMO patients exhibit increased expression of certain co-stimulatory molecules and production of IL-6.
Figure 5B:
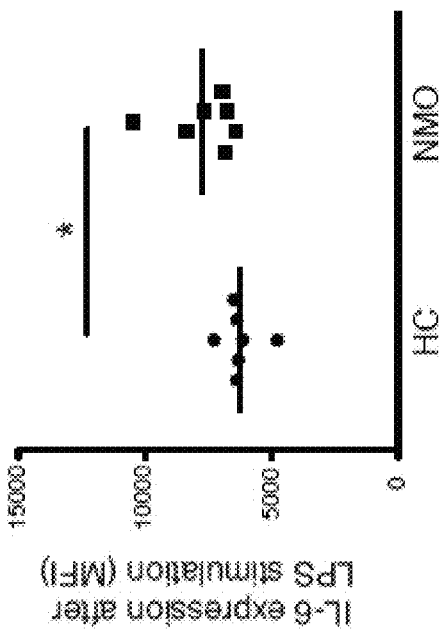
Figure 5C:
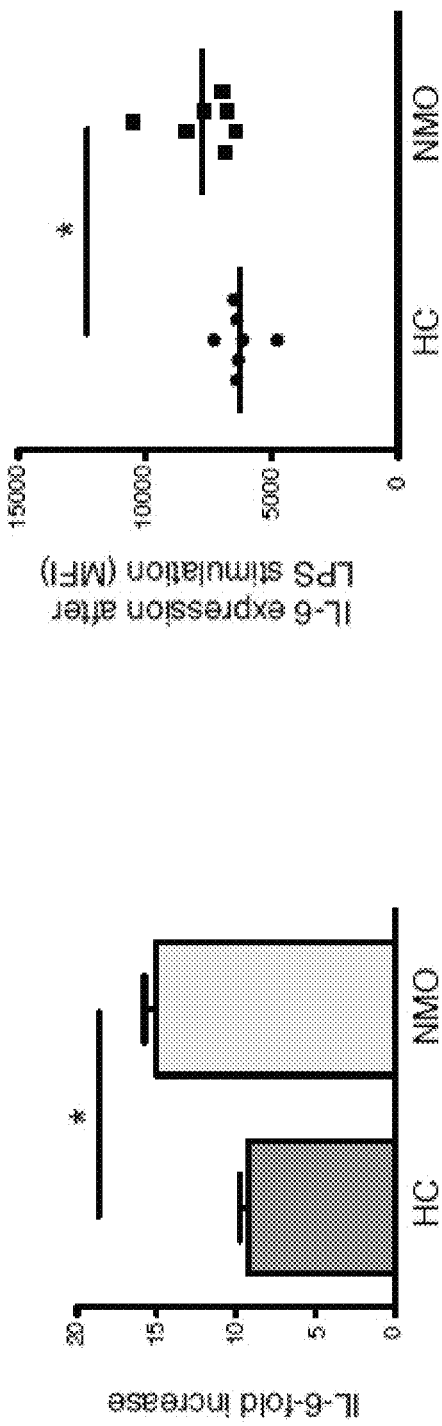

FIG. 5A-5C. CD14+ monocytes from NMO patients exhibit increased expression of certain co-stimulatory molecules and production of IL-6. (Panel A) PBMC were rested for 4 h at 37° C. Expression of co-stimulatory (CD80, CD86 and CD40) and MHC class II molecules was analyzed by FACS gating on the CD14+ population (n=8 NMO and n=8 HC). Isotype is indicated by grey histogram; healthy control and NMO patient histograms for expression of CD86 and HLA-DR were similar; for CD80 and CD40 expression the histogram for healthy control is present in between the histograms for isotype and NMO patient. As such, NMO patients exhibited a higher expression of CD80 and CD40 compared to healthy control. (Panels B and C) PBMC were stimulated with LPS (1 μg/ml) for 4 h. Expression of IL-6 in CD14+ monocytes was analyzed by ICS, before and after LPS stimulation. In (Panel C), horizontal lines indicate mean values; in (Panel A) and (Panel B) error bars represent SEM. *$P<0.05$, **$P<0.01$ Mann-Whitney test.

What is claimed is:

1. A composition comprising:
a peptide comprising a contiguous stretch of amino acids having the consensus amino acid sequence:

Leu-Pro-$X^1$-$X^2$-Met-$X^3$-$X^4$-Ile-$X^5$-$X^6$ (SEQ ID NO: 1)

wherein the peptide is up to 20 amino acids in length, and wherein
$X^1$ is Val (V) or Ile (I),
$X^2$ is Asp (D),
$X^3$ is Val (V), Ile (I), or Gly (G),
$X^4$ is Leu (L) or Ile (I),
$X^5$ is Met (M) or Ser (S),
and $X^6$ is Leu (L), Val (V), or Ala (A).

2. The composition of claim 1, wherein:
$X^1$ is Val (V),
$X^2$ is Asp (D),
$X^3$ is Val (V),
$X^4$ is Leu (L),
$X^5$ is Ser (S),
and $X^6$ is Leu (L).

3. A composition comprising:
a peptide comprising a contiguous stretch of amino acids having the consensus amino acid sequence:
LPVXMVLISL (SEQ ID NO:2)
wherein the peptide is up to 20 amino acids in length, and wherein X is Asp or Ser.

4. The composition of claim 1, wherein the peptide is 15-20 amino acids in length.

5. The composition of claim 1, wherein the peptide is 10-15 amino acids in length.

6. The composition of claim 3, wherein the peptide is 10-15 amino acids in length.

7. The composition of claim 1, further comprising a pharmaceutically acceptable carrier.

8. The composition of claim 3, further comprising a pharmaceutically acceptable carrier.

9. The composition of claim 1, further comprising a blood sample from a subject exhibiting symptoms of or being predisposed to neuromyelitis optica (NMO).

10. The composition of claim 1, further comprising T-cells obtained from a subject exhibiting symptoms of or being predisposed to neuromyelitis optica (NMO).

11. The composition of claim 3, further comprising a blood sample from a subject exhibiting symptoms of or being predisposed to neuromyelitis optica (NMO).

12. The composition of claim 3, further comprising T-cells obtained from a subject exhibiting symptoms of or being predisposed to neuromyelitis optica (NMO).

13. A method comprising:
    (a) contacting a sample from a subject with a peptide of claim 1; and
    (b) measuring number of T cells.

14. The method of claim 13, wherein the peptide is 10-30 amino acids in length.

15. A method of diagnosing Neuromyelitis Optica (NMO) in a subject, the method comprising:
    (a) contacting a sample from the subject with a peptide of claim 1; and
    (b) measuring the number of T cells, wherein an increase in the number of T cells as compared to a control indicates that the subject has NMO.

16. The method of claim 15, wherein the T cells are T helper 17 (Th17) T cells.

17. The method of claim 15, wherein the T cells are CD4$^+$ T cells.

18. The method of claim 15, wherein the peptide is 15-20 amino acids in length.

19. A method for screening for candidate agents for inhibiting proliferation of T cells, the method comprising:
    (a) contacting a T cell obtained from a subject having Neuromyelitis Optica with:
        (i) a peptide claim 1, and
        (ii) a candidate agent;
    (b) measuring the number of T cells, wherein a decrease in the number of T cells as compared to a control indicates that the candidate agent inhibits proliferation of T cells.

20. The method of claim 19, wherein the T cells are T helper 17 (Th17) T cells.

21. The method of claim 19, wherein the T cells are CD4$^+$ T cells.

22. The method of claim 19, wherein the peptide is 15-20 amino acids in length.

23. A method for inducing immune tolerance to AQP-4 protein and fragments thereof in a subject, the method comprising:
    administering an effective dose of the composition of claim 1 to a subject,
        wherein the administering the peptide induces immune tolerance to AQP-4 protein and fragments thereof in the subject.

24. The method of claim 23, wherein the peptide is 15-20 amino acids in length.

* * * * *

SEQUENCE LISTING

<160> NUMBER OF SEQ ID NOS: 25

<210> SEQ ID NO 1
<211> LENGTH: 10
<212> TYPE: PRT
<213> ORGANISM: Artificial Sequence
<220> FEATURE:
<223> OTHER INFORMATION: synthetic poypeptide
<220> FEATURE:
<221> NAME/KEY: MISC_FEATURE
<222> LOCATION: (3)..(3)
<223> OTHER INFORMATION: the amino acid at this position is Val (V) or Ile (I)
<220> FEATURE:
<221> NAME/KEY: MISC_FEATURE
<222> LOCATION: (4)..(4)
<223> OTHER INFORMATION: the amino acid at this position is Ser (S) or Asp (D)

```
<220> FEATURE:
<221> NAME/KEY: MISC_FEATURE
<222> LOCATION: (6)..(6)
<223> OTHER INFORMATION: the amino acid at this position is Val (V), Ile
      (I), or Gly (G)
<220> FEATURE:
<221> NAME/KEY: MISC_FEATURE
<222> LOCATION: (7)..(7)
<223> OTHER INFORMATION: the amino acid at this position is Leu (L) or
      Ile (I)
<220> FEATURE:
<221> NAME/KEY: MISC_FEATURE
<222> LOCATION: (9)..(9)
<223> OTHER INFORMATION: the amino acid at this position is Met (M) or
      Ser (S)
<220> FEATURE:
<221> NAME/KEY: MISC_FEATURE
<222> LOCATION: (10)..(10)
<223> OTHER INFORMATION: the amino acid at this position is Leu (L), Val
      (V), or Ala (A)

<400> SEQUENCE: 1

Leu Pro Xaa Xaa Met Xaa Xaa Ile Xaa Xaa
1               5                   10

<210> SEQ ID NO 2
<211> LENGTH: 10
<212> TYPE: PRT
<213> ORGANISM: Artificial sequence
<220> FEATURE:
<223> OTHER INFORMATION: synthetic poypeptide
<220> FEATURE:
<221> NAME/KEY: MISC_FEATURE
<222> LOCATION: (4)..(4)
<223> OTHER INFORMATION: the amino acid at this position is Asp or Ser

<400> SEQUENCE: 2

Leu Pro Val Xaa Met Val Leu Ile Ser Leu
1               5                   10

<210> SEQ ID NO 3
<211> LENGTH: 20
<212> TYPE: PRT
<213> ORGANISM: Artificial sequence
<220> FEATURE:
<223> OTHER INFORMATION: synthetic poypeptide

<400> SEQUENCE: 3

Gly Ile Leu Tyr Leu Val Thr Pro Pro Ser Val Val Gly Gly Leu Gly
1               5                   10                  15

Val Thr Met Val
            20

<210> SEQ ID NO 4
<211> LENGTH: 20
<212> TYPE: PRT
<213> ORGANISM: Artificial sequence
<220> FEATURE:
<223> OTHER INFORMATION: synthetic poypeptide

<400> SEQUENCE: 4

Ser Met Asn Pro Ala Arg Ser Phe Gly Pro Ala Val Ile Met Gly Asn
1               5                   10                  15

Trp Glu Asn His
            20

<210> SEQ ID NO 5
<211> LENGTH: 15
<212> TYPE: PRT
```

<213> ORGANISM: Artificial sequence
<220> FEATURE:
<223> OTHER INFORMATION: synthetic poypeptide

<400> SEQUENCE: 5

```
Ala Gly His Gly Leu Leu Val Glu Leu Ile Ile Thr Phe Gln Leu
1               5                   10                  15
```

<210> SEQ ID NO 6
<211> LENGTH: 20
<212> TYPE: PRT
<213> ORGANISM: Artificial sequence
<220> FEATURE:
<223> OTHER INFORMATION: synthetic poypeptide

<400> SEQUENCE: 6

```
Arg Phe Lys Glu Ala Phe Ser Lys Ala Ala Gln Gln Thr Lys Gly Ser
1               5                   10                  15

Tyr Met Glu Val
            20
```

<210> SEQ ID NO 7
<211> LENGTH: 14
<212> TYPE: PRT
<213> ORGANISM: Homo sapiens

<400> SEQUENCE: 7

```
Glu Lys Pro Leu Pro Val Asp Met Val Leu Ile Ser Leu Cys
1               5                   10
```

<210> SEQ ID NO 8
<211> LENGTH: 14
<212> TYPE: PRT
<213> ORGANISM: Clostridium perfringens

<400> SEQUENCE: 8

```
Phe Ile Ile Leu Pro Val Ser Met Val Leu Ile Ser Leu Val
1               5                   10
```

<210> SEQ ID NO 9
<211> LENGTH: 323
<212> TYPE: PRT
<213> ORGANISM: Homo sapiens

<400> SEQUENCE: 9

```
Met Ser Asp Arg Pro Thr Ala Arg Arg Trp Gly Lys Cys Gly Pro Leu
1               5                   10                  15

Cys Thr Arg Glu Asn Ile Met Val Ala Phe Lys Gly Val Trp Thr Gln
            20                  25                  30

Ala Phe Trp Lys Ala Val Thr Ala Glu Phe Leu Ala Met Leu Ile Phe
        35                  40                  45

Val Leu Leu Ser Leu Gly Ser Thr Ile Asn Trp Gly Gly Thr Glu Lys
    50                  55                  60

Pro Leu Pro Val Asp Met Val Leu Ile Ser Leu Cys Phe Gly Leu Ser
65                  70                  75                  80

Ile Ala Thr Met Val Gln Cys Phe Gly His Ile Ser Gly Gly His Ile
                85                  90                  95

Asn Pro Ala Val Thr Val Ala Met Val Cys Thr Arg Lys Ile Ser Ile
            100                 105                 110

Ala Lys Ser Val Phe Tyr Ile Ala Ala Gln Cys Leu Gly Ala Ile Ile
        115                 120                 125
```

```
Gly Ala Gly Ile Leu Tyr Leu Val Thr Pro Pro Ser Val Val Gly Gly
        130                 135                 140

Leu Gly Val Thr Met Val His Gly Asn Leu Thr Ala Gly His Gly Leu
145                 150                 155                 160

Leu Val Glu Leu Ile Ile Thr Phe Gln Leu Val Phe Thr Ile Phe Ala
                165                 170                 175

Ser Cys Asp Ser Lys Arg Thr Asp Val Thr Gly Ser Ile Ala Leu Ala
                180                 185                 190

Ile Gly Phe Ser Val Ala Ile Gly His Leu Phe Ala Ile Asn Tyr Thr
                195                 200                 205

Gly Ala Ser Met Asn Pro Ala Arg Ser Phe Gly Pro Ala Val Ile Met
210                 215                 220

Gly Asn Trp Glu Asn His Trp Ile Tyr Trp Val Gly Pro Ile Ile Gly
225                 230                 235                 240

Ala Val Leu Ala Gly Gly Leu Tyr Glu Tyr Val Phe Cys Pro Asp Val
                245                 250                 255

Glu Phe Lys Arg Arg Phe Lys Glu Ala Phe Ser Lys Ala Ala Gln Gln
                260                 265                 270

Thr Lys Gly Ser Tyr Met Glu Val Glu Asp Asn Arg Ser Gln Val Glu
                275                 280                 285

Thr Asp Asp Leu Ile Leu Lys Pro Gly Val Val His Val Ile Asp Val
290                 295                 300

Asp Arg Gly Glu Glu Lys Lys Gly Lys Asp Gln Ser Gly Glu Val Leu
305                 310                 315                 320

Ser Ser Val

<210> SEQ ID NO 10
<211> LENGTH: 618
<212> TYPE: PRT
<213> ORGANISM: Clostridium perfringens

<400> SEQUENCE: 10

Met Ser Lys Glu Arg Lys Gly Gly Met Gly Gly Pro Met Gly Arg Met
1               5                   10                  15

Gly Gly Gly Pro Arg Ala Val Glu Lys Ala Lys Asp Phe Lys Gly Thr
                20                  25                  30

Met Lys Lys Leu Gly Val Tyr Leu Lys Pro Tyr Ser Leu Ser Ile Ala
            35                  40                  45

Ile Val Ile Leu Phe Ala Ile Gly Ser Ala Ala Phe Ser Ile Val Gly
        50                  55                  60

Pro Lys Ile Leu Gly Lys Ala Thr Thr Lys Ile Phe Glu Gly Leu Val
65                  70                  75                  80

Gln Lys Ile Thr Gly Val Pro Asp Ala Ser Ile Asp Phe Gly Tyr Ile
                85                  90                  95

Gly Asn Ile Ala Met Ile Leu Val Ala Leu Tyr Leu Val Ser Ser Leu
                100                 105                 110

Phe Gly Ile Ile Gln Ser Phe Ile Met Ser Gly Val Ala Gln Lys Val
            115                 120                 125

Ser Tyr Asn Leu Arg Lys Gln Ile Ser Glu Lys Met Asp Thr Leu Pro
        130                 135                 140

Leu Asn Tyr Phe Asp Thr Arg Thr Asn Gly Glu Val Leu Ser Arg Ile
145                 150                 155                 160

Thr Asn Asp Val Asp Thr Val Asn Gln Thr Leu Asn Gln Ser Leu Ser
                165                 170                 175
```

```
Gln Ile Ile Thr Ser Val Val Thr Leu Ile Gly Val Leu Ile Met Met
                180                 185                 190
Phe Ser Ile Ser Trp Ile Met Thr Leu Ala Thr Phe Ile Ile Leu Pro
            195                 200                 205
Val Ser Met Val Leu Ile Ser Leu Val Val Lys Lys Ser Gln Lys Tyr
        210                 215                 220
Phe Lys Ser Gln Gln Glu Tyr Leu Gly His Leu Asn Gly Gln Val Glu
225                 230                 235                 240
Glu Val Tyr Gly Gly His Asn Ile Met Lys Ala Phe Asn Arg Glu Glu
                245                 250                 255
Ala Ser Thr Lys Asp Phe Asp Glu Leu Asn Asn Thr Leu Tyr Lys Ser
            260                 265                 270
Ala Trp Lys Ser Gln Phe Leu Ser Gly Met Met Met Pro Ile Met Ser
        275                 280                 285
Phe Val Gly Asn Leu Gly Tyr Val Leu Val Ser Ile Leu Gly Gly Trp
290                 295                 300
Leu Thr Ile Lys Ser Val Ile Thr Val Gly Asp Ile Gln Ala Phe Ile
305                 310                 315                 320
Gln Tyr Val Arg Ser Phe Asn Gln Pro Ile Ser Gln Met Ala Gln Val
                325                 330                 335
Ala Asn Ile Met Gln Ser Thr Ala Ala Ala Glu Arg Val Phe Glu
            340                 345                 350
Phe Leu Asp Glu Glu Asp Val Lys Asp Pro Val Asn Ser Val Asp
        355                 360                 365
Pro Ser Glu Ile Arg Gly Glu Val Glu Phe Asp Phe His Phe Gly
370                 375                 380
Tyr Asn Glu Asp Lys Ile Ile Ile Asn Asp Phe Ser Val Asp Val Lys
385                 390                 395                 400
Pro Gly Gln Lys Val Ala Ile Val Gly Pro Thr Gly Ala Gly Lys Thr
                405                 410                 415
Thr Ile Val Lys Leu Leu Met Arg Phe Tyr Asp Ile Asn Ser Gly Ser
            420                 425                 430
Ile Lys Ile Asp Gly His Asp Ile Arg Asp Phe Lys Arg Ala Asp Leu
        435                 440                 445
Arg Asn Leu Phe Gly Met Val Leu Gln Asp Thr Trp Leu Phe Asn Gly
450                 455                 460
Thr Ile Met Glu Asn Leu Arg Tyr Gly Arg Leu Asp Ala Thr Asp Ala
465                 470                 475                 480
Glu Val Lys Glu Ala Lys Ala Ala His Val Asp His Phe Val Lys
                485                 490                 495
Thr Leu Pro Asp Gly Tyr Asn Met Val Leu Asn Glu Glu Ala Ser Asn
            500                 505                 510
Ile Ser Gln Gly Gln Lys Gln Leu Leu Thr Ile Ala Arg Ala Phe Leu
        515                 520                 525
Lys Asp Pro Lys Leu Leu Ile Leu Asp Glu Ala Thr Ser Ser Val Asp
530                 535                 540
Thr Arg Thr Glu Leu Leu Ile Gln Lys Ala Met Glu Lys Leu Met Glu
545                 550                 555                 560
Gly Arg Thr Ser Phe Ile Ile Ala His Arg Leu Ser Thr Ile Arg Asp
                565                 570                 575
Ala Asp Leu Ile Leu Val Met Lys Asp Gly Asp Ile Val Glu Gln Gly
            580                 585                 590
Asn His Glu Glu Leu Leu Glu Lys Gly Gly Phe Tyr Ser Ser Leu Tyr
```

-continued

```
                595                 600                 605
Asn Ser Gln Phe Glu Gln Ser Ser Ala Ser
    610                 615

<210> SEQ ID NO 11
<211> LENGTH: 10
<212> TYPE: PRT
<213> ORGANISM: Homo sapiens

<400> SEQUENCE: 11

Leu Pro Val Asp Met Val Leu Ile Ser Leu
1               5                   10

<210> SEQ ID NO 12
<211> LENGTH: 10
<212> TYPE: PRT
<213> ORGANISM: Clostridium perfringens

<400> SEQUENCE: 12

Leu Pro Val Ser Met Val Leu Ile Ser Leu
1               5                   10

<210> SEQ ID NO 13
<211> LENGTH: 10
<212> TYPE: PRT
<213> ORGANISM: Clostridium scindens

<400> SEQUENCE: 13

Leu Pro Val Ser Met Gly Leu Ile Ser Val
1               5                   10

<210> SEQ ID NO 14
<211> LENGTH: 10
<212> TYPE: PRT
<213> ORGANISM: Clostridium sporogens

<400> SEQUENCE: 14

Leu Pro Val Ser Met Ile Ile Ile Met Leu
1               5                   10

<210> SEQ ID NO 15
<211> LENGTH: 10
<212> TYPE: PRT
<213> ORGANISM: Clostridium hylemonae

<400> SEQUENCE: 15

Leu Pro Ile Ser Met Gly Leu Ile Ser Ala
1               5                   10

<210> SEQ ID NO 16
<211> LENGTH: 10
<212> TYPE: PRT
<213> ORGANISM: Artificial sequence
<220> FEATURE:
<223> OTHER INFORMATION: synthetic poypeptide
<220> FEATURE:
<221> NAME/KEY: MISC_FEATURE
<222> LOCATION: (3)..(4)
<223> OTHER INFORMATION: the amino acid at this position may be any
      amino acid
<220> FEATURE:
<221> NAME/KEY: MISC_FEATURE
<222> LOCATION: (6)..(7)
<223> OTHER INFORMATION: the amino acid at this position may be any
      amino acid
<220> FEATURE:
<221> NAME/KEY: MISC_FEATURE
```

```
<222> LOCATION: (9)..(10)
<223> OTHER INFORMATION: the amino acid at this position may be any
      amino acid

<400> SEQUENCE: 16

Leu Pro Xaa Xaa Met Xaa Xaa Ile Xaa Xaa
1               5                   10

<210> SEQ ID NO 17
<211> LENGTH: 10
<212> TYPE: PRT
<213> ORGANISM: Artificial sequence
<220> FEATURE:
<223> OTHER INFORMATION: synthetic poypeptide
<220> FEATURE:
<221> NAME/KEY: MISC_FEATURE
<222> LOCATION: (4)..(4)
<223> OTHER INFORMATION: the amino acid at this position may be any
      amino acid

<400> SEQUENCE: 17

Leu Pro Val Xaa Met Val Leu Ile Ser Leu
1               5                   10

<210> SEQ ID NO 18
<211> LENGTH: 18
<212> TYPE: PRT
<213> ORGANISM: Artificial sequence
<220> FEATURE:
<223> OTHER INFORMATION: synthetic poypeptide

<400> SEQUENCE: 18

Gly Thr Glu Lys Pro Leu Pro Val Asp Met Val Leu Ile Ser Leu Cys
1               5                   10                  15

Phe Gly

<210> SEQ ID NO 19
<211> LENGTH: 16
<212> TYPE: PRT
<213> ORGANISM: Artificial sequence
<220> FEATURE:
<223> OTHER INFORMATION: synthetic poypeptide

<400> SEQUENCE: 19

Gly Thr Glu Lys Pro Leu Pro Val Asp Met Val Leu Ile Ser Leu Cys
1               5                   10                  15

<210> SEQ ID NO 20
<211> LENGTH: 14
<212> TYPE: PRT
<213> ORGANISM: Artificial sequence
<220> FEATURE:
<223> OTHER INFORMATION: synthetic poypeptide

<400> SEQUENCE: 20

Gly Thr Glu Lys Pro Leu Pro Val Asp Met Val Leu Ile Ser
1               5                   10

<210> SEQ ID NO 21
<211> LENGTH: 12
<212> TYPE: PRT
<213> ORGANISM: Artificial sequence
<220> FEATURE:
<223> OTHER INFORMATION: synthetic poypeptide

<400> SEQUENCE: 21

Gly Thr Glu Lys Pro Leu Pro Val Asp Met Val Leu
```

```
<210> SEQ ID NO 22
<211> LENGTH: 18
<212> TYPE: PRT
<213> ORGANISM: Artificial sequence
<220> FEATURE:
<223> OTHER INFORMATION: synthetic poypeptide

<400> SEQUENCE: 22

Glu Lys Pro Leu Pro Val Asp Met Val Leu Ile Ser Leu Cys Phe Gly
1               5                   10                  15

Leu Ser

<210> SEQ ID NO 23
<211> LENGTH: 16
<212> TYPE: PRT
<213> ORGANISM: Artificial sequence
<220> FEATURE:
<223> OTHER INFORMATION: synthetic poypeptide

<400> SEQUENCE: 23

Pro Leu Pro Val Asp Met Val Leu Ile Ser Leu Cys Phe Gly Leu Ser
1               5                   10                  15

<210> SEQ ID NO 24
<211> LENGTH: 14
<212> TYPE: PRT
<213> ORGANISM: Artificial sequence
<220> FEATURE:
<223> OTHER INFORMATION: synthetic poypeptide

<400> SEQUENCE: 24

Pro Val Asp Met Val Leu Ile Ser Leu Cys Phe Gly Leu Ser
1               5                   10

<210> SEQ ID NO 25
<211> LENGTH: 12
<212> TYPE: PRT
<213> ORGANISM: Artificial sequence
<220> FEATURE:
<223> OTHER INFORMATION: synthetic poypeptide

<400> SEQUENCE: 25

Asp Met Val Leu Ile Ser Leu Cys Phe Gly Leu Ser
1               5                   10
```